US009310909B2

(12) United States Patent
Myers et al.

(10) Patent No.: US 9,310,909 B2
(45) Date of Patent: Apr. 12, 2016

(54) METHODS, SYSTEMS AND DEVICES FOR PHYSICAL CONTACT ACTIVATED DISPLAY AND NAVIGATION

(71) Applicant: Fitbit, Inc., San Francisco, CA (US)

(72) Inventors: Nicholas Myers, Oakland, CA (US); Christine Brumback, San Francisco, CA (US); Timothy Roberts, San Francisco, CA (US); James Park, Berkeley, CA (US); Dave Knight, San Francisco, CA (US); Shelten Yuen, Berkeley, CA (US); Jayson Messenger, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/192,282

(22) Filed: Feb. 27, 2014

(65) Prior Publication Data
US 2014/0176475 A1 Jun. 26, 2014

Related U.S. Application Data

(60) Continuation-in-part of application No. 13/959,714, filed on Aug. 5, 2013, now Pat. No. 8,762,101, which is a continuation-in-part of application No. 13/693,334, filed on Dec. 4, 2012, now Pat. No.
(Continued)

(51) Int. Cl.
*G06F 3/041* (2006.01)
*G06F 19/00* (2011.01)
(Continued)

(52) U.S. Cl.
CPC .............. *G06F 3/041* (2013.01); *A61B 5/0022* (2013.01); *A61B 5/1118* (2013.01); *A61B 5/681* (2013.01);
(Continued)

(58) Field of Classification Search
CPC .............................. G01C 22/006; G06F 3/041
USPC ........................................... 702/160; 235/105
See application file for complete search history.

(56) References Cited

U.S. PATENT DOCUMENTS 2,717,736 A  9/1955  Schlesinger
2,883,255 A  4/1959  Anderson
(Continued)

FOREIGN PATENT DOCUMENTS

JP           11347021        12/1999
WO      WO 2008/038141       4/2008
WO      WO 2009/042965       4/2009

OTHER PUBLICATIONS

"Automatic classification of ambulatory movements and evaluation of energy consumptions utilizing accelerometers and barometer", Ohtaki, et al, Microsystem Technologies, vol. 11, No. 8-10, Aug. 2005, pp. 1034-1040.
(Continued)

*Primary Examiner* — Toan Le
*Assistant Examiner* — Manuel Rivera Vargas
(74) *Attorney, Agent, or Firm* — Martine Penilla Group, LLP

(57) ABSTRACT

Methods, systems and devices are provided for providing user interface navigation of screen display metrics of a device. In one example, a device is configured for capture of activity data for a user. The device includes a housing and a screen disposed on the housing to display a plurality of metrics which include metrics that characterize the activity captured over time. The device further includes a sensor disposed in the housing to capture physical contact upon the housing. A processor is included to process the physical contact to determine if the physical contact qualifies as an input. The processor enables the screen from an off state when the physical contact qualifies as the input. The screen is configured to display one or more of the plurality of metrics in accordance with a scroll order, and a first metric displayed in response to the physical contact that qualifies as the input.

28 Claims, 15 Drawing Sheets

Related U.S. Application Data 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, now Pat. No. 9,167,991, application No. 14/192,282, filed on Feb. 27, 2014, which is a continuation-in-part of application No. 13/959,714, filed on Aug. 5, 2013, now Pat. No. 8,762,101, which is a continuation-in-part of application No. 13/759,485, filed on Feb. 5, 2013, now Pat. No. 8,543,351, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, now Pat. No. 9,167,991, application No. 14/192,282, filed on Feb. 27, 2014, which is a continuation-in-part of application No. 13/913,726, filed on Jun. 10, 2013, now Pat. No. 8,670,953, and a continuation of application No. 14/050,270, filed on Oct. 9, 2013, now abandoned.

(60) Provisional application No. 61/388,595, filed on Sep. 30, 2010, provisional application No. 61/390,811, filed on Oct. 9, 2010, provisional application No. 61/885,959, filed on Oct. 2, 2013.

(51) Int. Cl.

| | |
|---|---|
| A61B 5/00 | (2006.01) |
| A61B 5/0205 | (2006.01) |
| A61B 5/021 | (2006.01) |
| A61B 5/024 | (2006.01) |
| A61B 5/11 | (2006.01) |
| A61B 5/22 | (2006.01) |
| G01C 22/00 | (2006.01) |

(52) U.S. Cl.
CPC .............. *G06F 19/3406* (2013.01); *A61B 5/021* (2013.01); *A61B 5/024* (2013.01); *A61B 5/02055* (2013.01); *A61B 5/1112* (2013.01); *A61B 5/1123* (2013.01); *A61B 5/222* (2013.01); *A61B 5/4809* (2013.01); *A61B 5/4812* (2013.01); *A61B 5/4815* (2013.01); *A61B 5/6838* (2013.01); *A61B 2560/0214* (2013.01); *A61B 2560/0242* (2013.01); *A61B 2562/0219* (2013.01); *G01C 22/006* (2013.01); *G06F 19/3481* (2013.01)

(56) References Cited

U.S. PATENT DOCUMENTS

| | | | |
|---|---|---|---|
| 3,163,856 A | 12/1964 | Kirby | |
| 3,250,270 A | 5/1966 | Lyon Bloom | |
| 3,918,658 A | 11/1975 | Beller | |
| 4,192,000 A | 3/1980 | Lipsey | |
| 4,244,020 A | 1/1981 | Ratcliff | |
| 2,284,849 A | 8/1981 | Anderson et al. | |
| 4,281,663 A | 8/1981 | Pringle | |
| 4,284,849 A | 8/1981 | Anderson et al. | |
| 4,312,358 A | 1/1982 | Barney | |
| 4,367,752 A | 1/1983 | Jimenez et al. | |
| 4,390,922 A | 6/1983 | Pelliccia | |
| 4,407,295 A | 10/1983 | Steuer et al. | |
| 4,425,921 A | 1/1984 | Fujisaki et al. | |
| 4,575,804 A | 3/1986 | Ratcliff | |
| 4,578,769 A | 3/1986 | Frederick | |
| 4,617,525 A | 10/1986 | Lloyd | |
| 4,887,249 A * | 12/1989 | Thinesen ................... 368/10 |
| 4,977,509 A | 12/1990 | Pitchford et al. | |
| 5,058,427 A | 10/1991 | Brandt | |
| 5,224,059 A | 6/1993 | Nita et al. | |
| 5,295,085 A | 3/1994 | Hoffacker | |
| 5,323,650 A | 6/1994 | Fullen et al. | |
| 5,446,705 A | 8/1995 | Haas et al. | |
| 5,456,648 A | 10/1995 | Edinburg et al. | |
| 5,553,296 A * | 9/1996 | Forrest et al. ................. 713/323 |
| 5,583,776 A | 12/1996 | Levi et al. | |
| 5,671,162 A | 9/1997 | Werbin | |
| 5,704,350 A | 1/1998 | Williams, III | |
| 5,724,265 A | 3/1998 | Hutchings | |
| 5,890,128 A | 3/1999 | Diaz et al. | |
| 5,891,042 A | 4/1999 | Sham et al. | |
| 5,894,454 A | 4/1999 | Kondo | |
| 5,899,963 A | 5/1999 | Hutchings | |
| 5,947,868 A | 9/1999 | Dugan | |
| 5,955,667 A | 9/1999 | Fyfe | |
| 5,976,083 A | 11/1999 | Richardson et al. | |
| 6,018,705 A | 1/2000 | Gaudet et al. | |
| 6,077,193 A | 6/2000 | Buhler et al. | |
| 6,085,248 A | 7/2000 | Sambamurthy et al. | |
| 6,129,686 A | 10/2000 | Friedman | |
| 6,145,389 A | 11/2000 | Ebeling et al. | |
| 6,183,425 B1 | 2/2001 | Whalen et al. | |
| 6,213,872 B1 | 4/2001 | Harada et al. | |
| 6,241,684 B1 | 6/2001 | Amino et al. | |
| 6,287,262 B1 | 9/2001 | Amano et al. | |
| 6,301,964 B1 | 10/2001 | Fyfe et al. | |
| 6,302,789 B2 | 10/2001 | Harada et al. | |
| 6,305,221 B1 | 10/2001 | Hutchings | |
| 6,309,360 B1 | 10/2001 | Mault | |
| 6,469,639 B2 | 10/2002 | Tanenhaus et al. | |
| 6,478,736 B1 | 11/2002 | Mault | |
| 6,513,381 B2 | 2/2003 | Fyfe et al. | |
| 6,513,532 B2 | 2/2003 | Mault et al. | |
| 6,527,711 B1 | 3/2003 | Stivoric et al. | |
| 6,529,827 B1 | 3/2003 | Beason et al. | |
| 6,561,951 B2 | 5/2003 | Cannon et al. | |
| 6,571,200 B1 | 5/2003 | Mault | |
| 6,585,622 B1 | 7/2003 | Shum et al. | |
| 6,607,493 B2 | 8/2003 | Song | |
| 6,620,078 B2 | 9/2003 | Pfeffer | |
| 6,678,629 B2 | 1/2004 | Tsuji | |
| 6,699,188 B2 | 3/2004 | Wessel | |
| 6,761,064 B2 | 7/2004 | Tsuji | |
| 6,790,178 B1 | 9/2004 | Mault et al. | |
| 6,808,473 B2 | 10/2004 | Hisano et al. | |
| 6,811,516 B1 | 11/2004 | Dugan | |
| 6,813,582 B2 | 11/2004 | Levi et al. | |
| 6,813,931 B2 | 11/2004 | Yadav et al. | |
| 6,856,938 B2 | 2/2005 | Kurtz | |
| 6,862,575 B1 | 3/2005 | Anttila et al. | |
| 7,062,225 B2 | 6/2006 | White | |
| 7,162,368 B2 | 1/2007 | Levi et al. | |
| 7,171,331 B2 | 1/2007 | Vock et al. | |
| 7,200,517 B2 | 4/2007 | Darley et al. | |
| 7,246,033 B1 | 7/2007 | Kudo | |
| 7,261,690 B2 | 8/2007 | Teller et al. | |
| 7,272,982 B2 | 9/2007 | Neuhauser et al. | |
| 7,373,820 B1 | 5/2008 | James | |
| 7,443,292 B2 | 10/2008 | Jensen et al. | |
| 7,457,724 B2 | 11/2008 | Vock et al. | |
| 7,467,060 B2 | 12/2008 | Kulach et al. | |
| 7,505,865 B2 | 3/2009 | Ohkubo et al. | |
| 7,559,877 B2 * | 7/2009 | Parks et al. ................. 482/8 |
| 7,653,508 B1 | 1/2010 | Kahn et al. | |
| 7,690,556 B1 | 4/2010 | Kahn et al. | |
| 7,713,173 B2 | 5/2010 | Shin et al. | |
| 7,762,952 B2 | 7/2010 | Lee et al. | |
| 7,774,156 B2 | 8/2010 | Niva et al. | |
| 7,789,802 B2 | 9/2010 | Lee et al. | |
| 7,881,902 B1 | 2/2011 | Kahn et al. | |
| 7,927,253 B2 | 4/2011 | Vincent et al. | |

(56) References Cited

U.S. PATENT DOCUMENTS

| | | |
|---|---|---|
| 7,983,876 B2 | 7/2011 | Vock et al. |
| 8,028,443 B2 | 10/2011 | Case, Jr. |
| 8,055,469 B2 | 11/2011 | Kulach et al. |
| 8,099,318 B2 | 1/2012 | Moukas et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,463,576 B2 | 6/2013 | Yuen et al. |
| 8,463,577 B2 | 6/2013 | Yuen et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,583,402 B2 | 11/2013 | Yuen et al. |
| 8,597,093 B2 | 12/2013 | Engelberg et al. |
| 8,670,953 B2 | 3/2014 | Yuen et al. |
| 2001/0055242 A1 | 12/2001 | Deshmuhk et al. |
| 2002/0013717 A1 | 1/2002 | Ando et al. |
| 2002/0077219 A1 | 6/2002 | Cohen et al. |
| 2002/0082144 A1 | 6/2002 | Pfeffer |
| 2002/0109600 A1 | 8/2002 | Mault et al. |
| 2002/0178060 A1 | 11/2002 | Sheehan |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0061324 A1 | 4/2004 | Howard |
| 2004/0117963 A1 | 6/2004 | Schneider |
| 2004/0152957 A1 | 8/2004 | Stivoric et al. |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0089542 A1 | 4/2006 | Sands |
| 2006/0111944 A1 | 5/2006 | Sirmans, Jr. et al. |
| 2006/0129436 A1 | 6/2006 | Short |
| 2006/0143645 A1 | 6/2006 | Vock et al. |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0071643 A1 | 3/2007 | Hall et al. |
| 2007/0123391 A1 | 5/2007 | Shin et al. |
| 2007/0136093 A1 | 6/2007 | Rankin et al. |
| 2007/0155277 A1 | 7/2007 | Amitai et al. |
| 2007/0159926 A1* | 7/2007 | Prstojevich et al. ............ 368/10 |
| 2007/0179356 A1 | 8/2007 | Wessel |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2008/0093838 A1 | 4/2008 | Tropper et al. |
| 2008/0125288 A1 | 5/2008 | Case |
| 2008/0140163 A1 | 6/2008 | Keacher et al. |
| 2008/0140338 A1 | 6/2008 | No et al. |
| 2009/0018797 A1 | 1/2009 | Kasama et al. |
| 2009/0043531 A1 | 2/2009 | Kahn et al. |
| 2009/0048044 A1 | 2/2009 | Oleson et al. |
| 2009/0054737 A1 | 2/2009 | Magar et al. |
| 2009/0063193 A1 | 3/2009 | Barton et al. |
| 2009/0171788 A1 | 7/2009 | Tropper et al. |
| 2009/0271147 A1* | 10/2009 | Sugai ............................ 702/160 |
| 2010/0205541 A1 | 8/2010 | Rapaport et al. |
| 2010/0217099 A1 | 8/2010 | LeBoeuf et al. |
| 2011/0003665 A1 | 1/2011 | Burton et al. |
| 2011/0009051 A1 | 1/2011 | Khedouri et al. |
| 2011/0022349 A1 | 1/2011 | Stirling et al. |
| 2011/0080349 A1* | 4/2011 | Holbein et al. ............... 345/173 |
| 2011/0106449 A1 | 5/2011 | Chowdhary et al. |
| 2011/0131005 A1 | 6/2011 | Ueshima et al. |
| 2011/0193704 A1* | 8/2011 | Harper et al. .............. 340/573.1 |
| 2011/0224508 A1 | 9/2011 | Moon |
| 2011/0230729 A1 | 9/2011 | Shirasaki et al. |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0183939 A1 | 7/2012 | Aragones et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265480 A1 | 10/2012 | Oshima |
| 2012/0330109 A1 | 12/2012 | Tran |
| 2013/0006718 A1 | 1/2013 | Nielsen et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0095459 A1 | 4/2013 | Tran |
| 2013/0096843 A1 | 4/2013 | Yuen et al. |
| 2013/0151196 A1 | 6/2013 | Yuen et al. |
| 2013/0158369 A1 | 6/2013 | Yuen et al. |
| 2013/0231574 A1 | 9/2013 | Tran |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0296666 A1 | 11/2013 | Kumar et al. |
| 2013/0296673 A1 | 11/2013 | Thaveeprungsriporn et al. |
| 2013/0310896 A1 | 11/2013 | Mass |
| 2013/0325396 A1 | 12/2013 | Yuen et al. |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0077673 A1 | 3/2014 | Garg et al. |

OTHER PUBLICATIONS

"Activity Classification Using Realistic Data From Wearable Sensors", Parkka, et al, IEEE Transactions on Information Technology in Biomedicine, vol. 10, No. 1, Jan. 2006, pp. 119-128.

"Indoor Navigation with MEMS Sensors", Lammel, et al., Proceedings of the Eurosensors XIII conference, vol. 1, No. 1, Sep. 2009, pp. 532-535.

"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.

"On Foot Navigation: When GPS alone is not Enough", Ladetto, et al, Journal of Navigation, vol. 53, No. 2, Sep. 2000, pp. 279-285.

"A Hybrid Discriminative/Generative Approach for Modeling Human Activities", Lester, et al., Proc. of the Int'l Joint Conf. Artificial Intelligence, 2005, pp. 766-772.

"Using MS5534 for altimeters and barometers", Intersema App., Note AN501, Jan. 2006.

"Validated caloric expenditure estimation using a single body-worn sensor", Lester, et al, Proc. of the Int'l Conf. on Ubiquitous Computing, 2009, pp. 225-234.

"Drift-free dynamic height sensor using MEMS IMU aided by MEMS pressure sensor", Tanigawa, et al, Workshop on Positioning, Navigation and Communication, Mar. 2008, pp. 191-196.

(56) References Cited

OTHER PUBLICATIONS

"Improvement of Walking Speed Prediction by Accelerometry and Altimetry, Validated by Satellite Positioning", Perrin, et al, Medical & Biological Engineering & Computing, vol. 38, 2000, pp. 164-168.

"An Intelligent Multi-Sensor system for Pedestrian Navigation", Retscher, Journal of Global Positioning Systems, vol. 5, No. 1, 2006, pp. 110-118.

"Evaluation of a New Method of Heading Estimation of Pedestrian Dead Reckoning Using Shoe Mounted Sensors", Stirling et al., Journal of Navigation, vol. 58, 2005, pp. 31-45.

"Direct Measurement of Human Movement by Accelerometry", Godfrey, et al., Medical Engineering & Physics, vol. 30, 2008, pp. 1364-1386.

"Foot Mounted Inertia System for Pedestrian Naviation", Godha et al., Measurement Science and Technology, vol. 19, No. 7, May 2008, pp. 1-9.

"Altimeter and Barometer System", Clifford, et al., Freescale Semiconductor Aplication Note AN1979, Rev. 3, Nov. 2006.

"SCP 1000-D01/D11 Pressure Sensor as Barometer and Altimeter", VTI Technologies Application, Jun. 2006, Note 33.

"Suunto LUMI User Guide", Jun. and Sep. 1997.

International Search Report issued on Aug. 15, 2008, in related application PCT/IB07/03617.

Deepak et al., Plug-and-Play, Single-Chip Photoplethysmography, 34th Annual International Conference of the IEEE EMBS, San Diego, California USA, Aug. 28-Sep. 1, 2012, 4 pages.

* cited by examiner

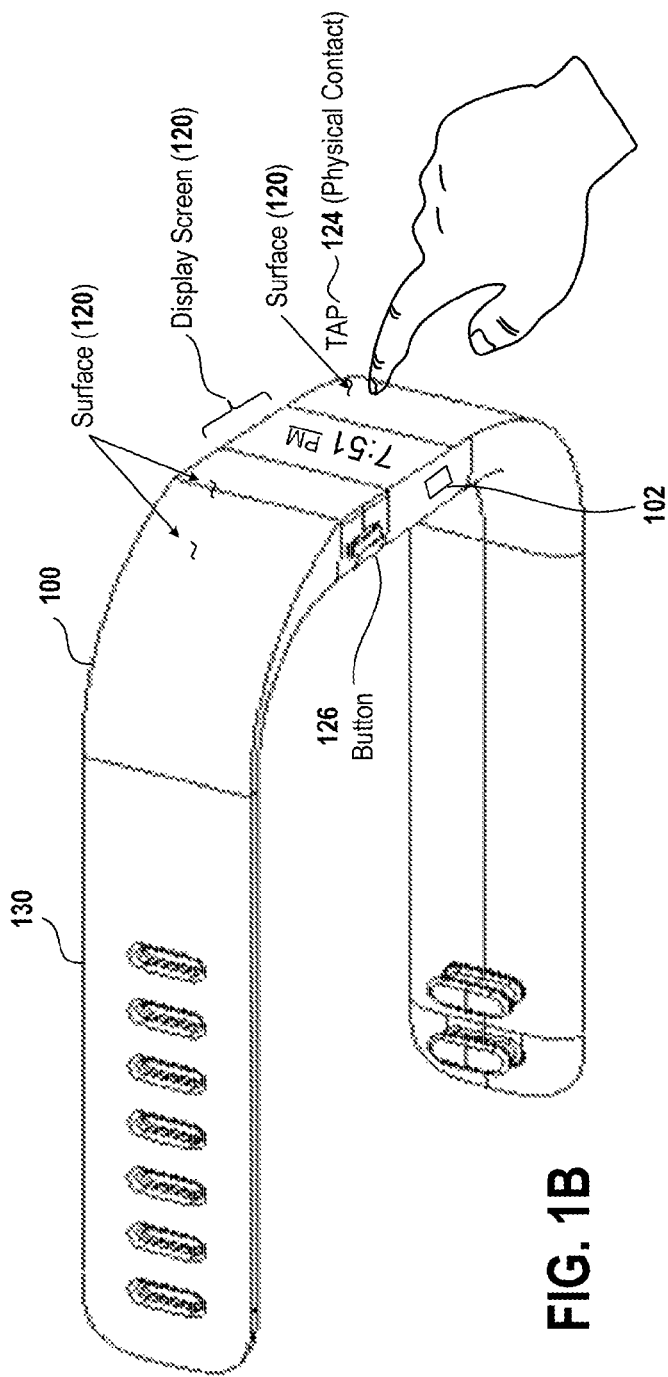
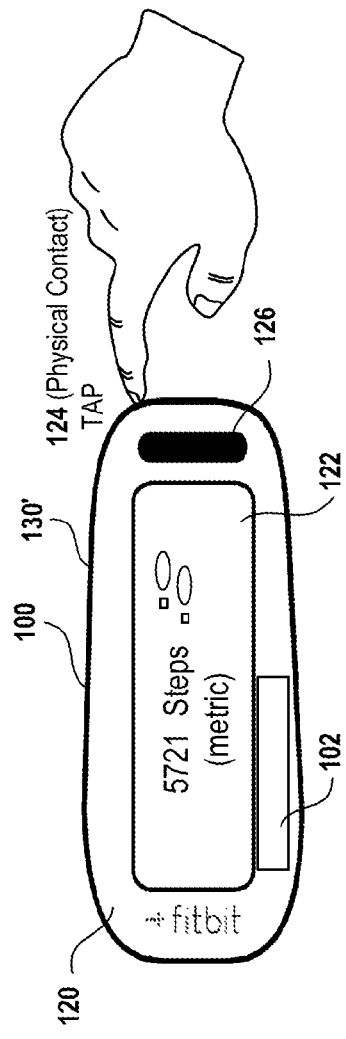
FIG. 1B
FIG. 1C

FIG. 3F    FIG. 3G

(Screen Off)
Mode: Ready

(Screen Off)
Mode: First Metric

(Screen Off)
Mode: Next Metric

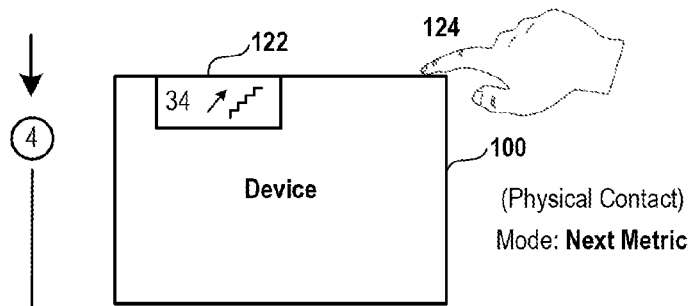
(Physical Contact)
Mode: Next Metric   FIG. 4A-4
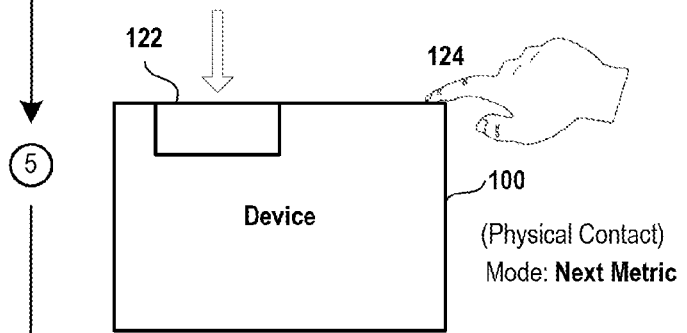
(Physical Contact)
Mode: Next Metric   FIG. 4A-5
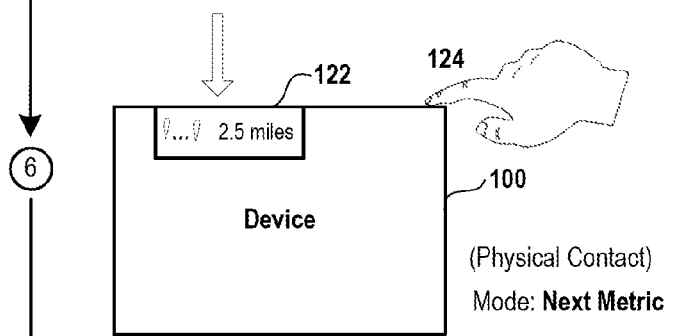
(Physical Contact)
Mode: Next Metric   FIG. 4A-6
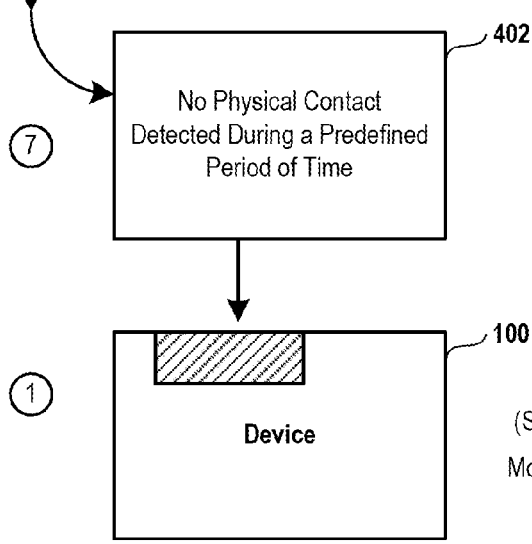
FIG. 4A-7
(Screen Off)
Mode: Ready   FIG. 4A-8

| Scroll Order (Configuration) | | Input |
|---|---|---|
| ① Screen Off | Ready (power saving) | No physical contact qualifying as input |
| ② Time of Day | (First Metric) "Home" | Double Tap (DT) |
| ③ Step Count | (Next Metric) | Double Tap (DT) |
| ④ Stairs Count | (Next Metric) | Double Tap (DT) |
| ⑤ Calories Burned | (Next Metric) | Double Tap (DT) |
| ⑥ Distance | (Last Metric) | Double Tap (DT) |

METHODS, SYSTEMS AND DEVICES FOR PHYSICAL CONTACT ACTIVATED DISPLAY AND NAVIGATION

CLAIM OF PRIORITY

This application is a continuation of U.S. patent application Ser. No. 14/050,270, entitled "Methods, Systems and Devices for Physical Contact Activated Display and Navigation", filed on Oct. 10, 2013, which claims priority to U.S. Provisional Application No. 61/885,959, entitled "Methods, Systems and Devices for Physical Contact Activated Display and Navigation", filed on Oct. 2, 2013, each of which is incorporated herein by reference.

This application is a continuation-in-part of U.S. patent application Ser. No. 13/959,714, filed on Aug. 5, 2013, titled "Methods and Systems for Identification of Event Data Having Combined Activity and Location Information of Portable Monitoring Devices", which is a continuation-in-part of U.S. patent application Ser. No. 13/693,334 (now issued as U.S. Pat. No. 8,548,770, issued on Oct. 1, 2013), filed on Dec. 4, 2012, titled "Portable Monitoring Devices and Methods for Operating Same", which is a divisional of U.S. patent application Ser. No. 13/667,229 (now issued as U.S. Pat. No. 8,437,980, issued on May 7, 2013), filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same", and to U.S. Provisional Patent Application No. 61/390,811, filed on Oct. 7, 2010, and titled "Portable Monitoring Devices and Methods for Operating Same", all of which are hereby incorporated by reference in their entirety.

This application is a continuation-in-part of Ser. No. 13/959,714, filed Aug. 5, 2013, titled "Methods and Systems for Identification of Event Data Having Combined Activity and Location Information of Portable Monitoring Devices", which is a continuation-in-part of U.S. patent application Ser. No. 13/759,485, (now issued as U.S. Pat. No. 8,543,351, issued on Sep. 24, 2013), filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

This application is a continuation-in-part of U.S. patent application Ser. No. 13/913,726, filed on Jun. 10, 2013, titled "Portable Monitoring Devices and Methods for Operating Same", which is incorporated by reference in its entirety.

FIELD

The present disclosure relates to systems and methods for capturing activity data over a period of time and methods and systems for navigating metric data to a display.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness trackers are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data with complicated or confusing interfaces.

It is in this context that embodiments described herein arise.

SUMMARY

Embodiments described in the present disclosure provide systems, apparatus, computer readable media, and methods for analyzing tracked activity data and providing navigation screens and interfaces on a device used by a user. The activity tracking device includes sensor(s) for detecting when physical contact occurs onto the activity tracking device and logic for providing a display action to the screen of the activity tracking device. The physical contact, in one embodiment, can be qualified as an input when the physical contact has a particular characteristic or pattern that is predefined. The characteristic can be, when the contact is the result of one or more taps, e.g., physical contact to the activity tracking device by a finger or hand of the user, or object held by a user and used to impart the contact.

In one embodiment, a method is provided. The method includes detecting a physical contact by a sensor of a device that is configured to display a plurality of metrics on a screen of the device and examining the physical contact to determine if the physical contact qualifies as an input for the device. The method acts to maintain the screen of the device in an off state for physical contact that does not qualify as the input and actives the screen of the device to display a first metric when the examining determines that the physical contact qualifies as the input. The method is executed by a processor.

In another embodiment, a device configured for capture of activity data for a user is provided. The device includes a housing and a screen disposed on the housing to display a plurality of metrics which include metrics that characterize the activity captured over time. The device further includes a sensor disposed in the housing to capture physical contact upon the housing. A processor is included to process the physical contact to determine if the physical contact qualifies as an input. The processor enables the screen from an off state when the physical contact qualifies as the input. The screen is configured to display one or more of the plurality of metrics in accordance with a scroll order, and a first metric of the plurality of metrics is displayed in accordance with user configuration identifying that the first metric is to be displayed in response to the physical contact that qualifies as the input, as determined by the processor.

In another embodiment, computer readable medium for storing program instructions executable by a processor is provided. The computer readable medium includes (a) program instructions for detecting a physical contact by a sensor of a device that is configured to display a plurality of metrics on a screen of the device; (b) program instructions for examining the physical contact to determine if the physical contact qualifies as an input for the device; (c) program instructions for maintaining the screen of the device in an off state for physical contact that does not qualify as the input; (d) program instructions for activating the screen of the device to display a first metric when the examining determines that the physical contact qualifies as the input, (e) program instructions for detecting user input to transition from the first metric to a next metric in a scroll order or to an off state when no user input is detected. If user input is received within a predetermined time after the off state, a process turns the screen on and displays the last displayed metric, and if the user input is received after the predetermined time after the off state, a process turns the screen on and displays the first metric. The plurality of metrics include a time of day metric and metrics representing activity data captured by the device when associated with a user, the activity data being of the user.

In some embodiments, the input is associated with qualified physical contact, and the user input is associated with one of qualified physical contact, or non-touch proximity input, or voice input, or button press input.

In still another embodiment, an activity tracking device is configured for capturing data or activity data for a user. The device includes a housing configured as a wearable wrist attachable structure or a structure that can accompany the user to capture the activity data. The device includes a screen disposed on the housing to display a plurality of metrics which include metrics that characterize the activity captured over time. The device has an accelerometer sensor disposed in the housing to capture physical contact upon the housing. The device further includes a processor to process the physical contact to determine if the physical contact qualifies as an input. The processor enables the screen from an off state when the physical contact qualifies as the input, and the screen is configured to display one or more of the plurality of metrics in accordance with a scroll order. A first metric of the plurality of metrics is displayed in accordance with user configuration identifying that the first metric is to be displayed in response to the physical contact that qualifies as the input, as determined by the processor. The physical contact captured by the accelerometer sensor is from sensing or detecting one or more taps having a predefined tap profile upon the housing by a finger, or hand or object. The user configuration identifying the first metric enables setting of a shortcut to any metric in the scroll order to be the first metric.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings.

FIG. 1B illustrates an example of an activity tracking device, in accordance with one embodiment of the present invention.

FIG. 1C illustrates another example of an activity tracking device, in accordance with one embodiment of the present invention.

FIG. 3F illustrates an example of the scroll order that extends from metric 1 to metric 4, in accordance with one embodiment of the present invention.

FIG. 3G illustrates an example where metric 3 is designated as the first metric, which will be the metric data displayed initially upon receiving the double tap input.

FIG. 4A-2 illustrates an example in accordance with an alternative embodiment, associated with navigating the screens of an activity tracking device showing a first metric.

FIG. 4A-3 illustrates an example in accordance with an alternative embodiment, associated with navigating the screens of an activity tracking device showing a next metric.

FIG. 4A-4 illustrates an example in accordance with an alternative embodiment, associated with navigating the screens of an activity tracking device showing a next metric.

FIG. 4A-5 illustrates an example in accordance with an alternative embodiment, associated with navigating the screens of an activity tracking device showing a next metric.

FIG. 4A-6 illustrates an example in accordance with an alternative embodiment, associated with navigating the screen of an activity tracking device showing a next metric.

FIG. 4A-7 illustrates an example in accordance with an alternative embodiment, associated with navigating the screens of an activity tracking device showing no physical contact.

FIG. 4A-8 illustrates an example in accordance with an alternative embodiment, associated with navigating the screens of an activity tracking device showing a ready mode.

FIG. 5 illustrates a table providing a scroll order and the various inputs that can be defined to traversed the scroll order, in one embodiment.

FIG. 6 illustrates an example of a physical contact represented by tap(s), which act to activate the display in a first metric, in accordance with one embodiment of the present invention.

FIG. 7 illustrates another example where a single tap activates the display in the first metric, in accordance with one embodiment of the present invention.

FIG. 8 illustrates an example of a double tap physical contact acting to initiate the display with the first metric, in accordance with one embodiment of the present invention.

DETAILED DESCRIPTION

Embodiments described in the present disclosure provide systems, apparatus, computer readable media, and methods for analyzing tracked activity data and providing navigation screens and interfaces. Some embodiments are directed to providing navigation interfaces for an activity tracking device. The activity tracking device includes sensors for detecting when physical contact occurs onto the activity tracking device and logic for providing a display action to the screen of the activity tracking device. The physical contact, in one embodiment, can be qualified as an input when the physical contact has a particular characteristic that is predefined. The characteristic can be, when the contact is the result of one or more taps, e.g., physical contact to the activity tracking device by a finger or hand of the user, or object held by a user and used to impart the contact.

In other embodiments, the input can be non-physical, such as proximity sensing input. The proximity sensing input can be processed by an infrared proximity sensor, a thermal sensor, etc. The input can also be by way of a button, voice input, gaze detected input, input processed in response to motion or motion profiles, etc.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

Figure 1A:
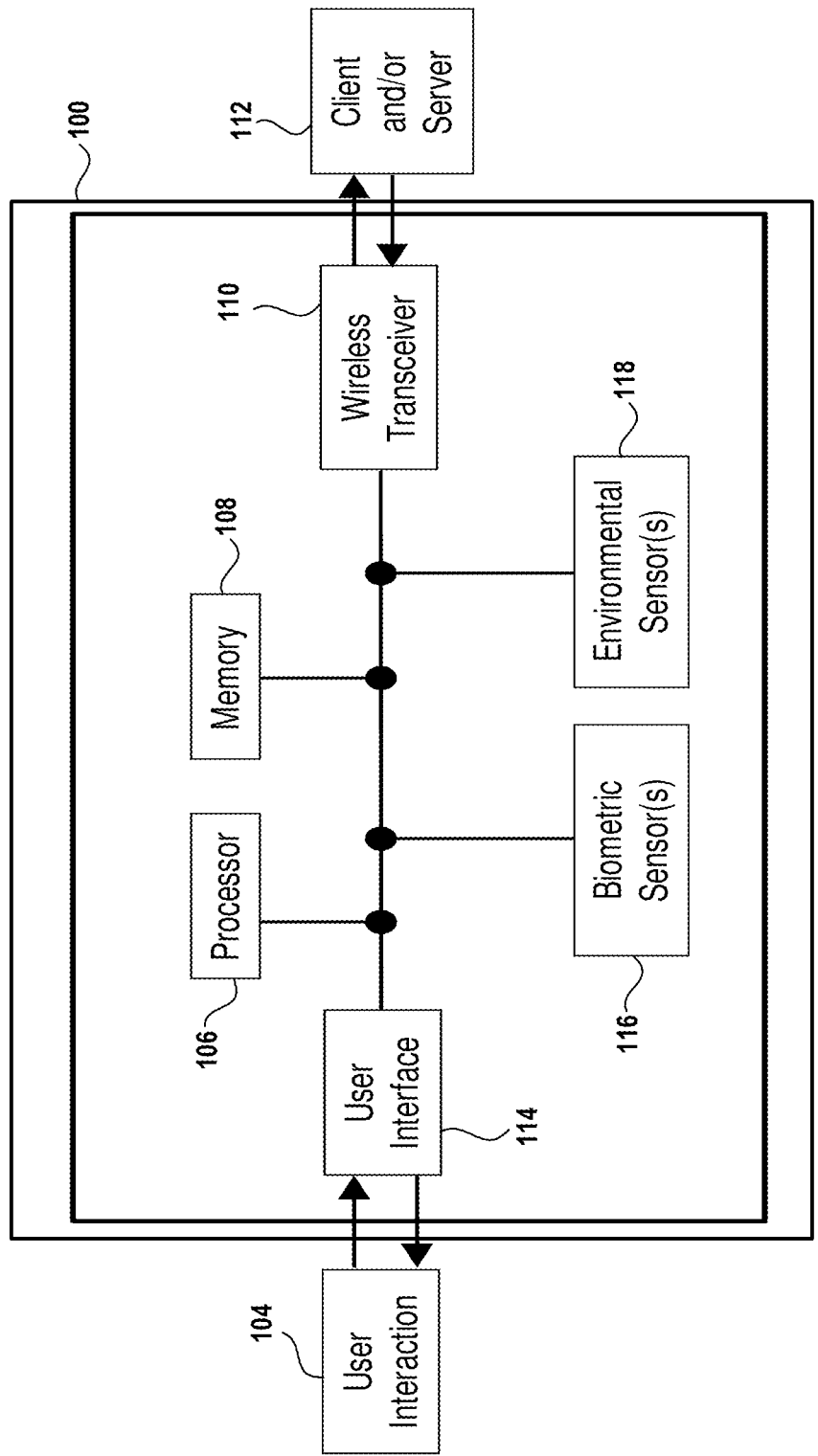
FIG. 1A shows a block diagram of an activity tracking device, in accordance with one embodiment of the present invention.

FIG. 1A shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.).

In some embodiments, the user interface 114 is configured to receive user interaction 104 that is in the form of noncontact input. The noncontact input can be by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. As will be explained in more detail below, the physical contact may be in the form of a tap or multiple taps by a finger upon the housing of the activity tracking device 100.

FIG. 1B illustrates an example of an activity tracking device 100 having a housing 130 in the form of a wearable wrist attachable device. The sensors of the activity tracking device 100 can, as mentioned above, detect motion such as physical contact that is applied and received on a surface 120 of the housing 130. In the example shown, the physical contact 124 is in the form of a tap or multiple taps on the surface 120. Device components 102 are, in one embodiment, contained within the housing 130. The location at which the device components 102 are integrated into the housing 130 can vary. For example, the device components 102 can be integrated throughout various locations around the housing 130, and not limited to the central portion of the wrist attachable device. In some embodiments, the device components 102 can be integrated into or with a smart watch device.

In other embodiments, the device components 102 are positioned substantially in a central position of the wrist attachable device, such as under or proximate to a location where a display screen 122 is located. In the illustrated example, the housing 130 also includes a button 126. The button 126 can be pressed to activate the display screen 122, navigate to various metrics displayed on the screen 122, or turn off the screen 122.

FIG. 1C illustrates another example of an activity tracking device 100, in accordance with one embodiment of the present invention. The form factor of the activity tracking device 100 is shown as a clickable device that includes a screen 122, a button 126, and device components 102 integrated within the housing 130'. The housing 130' can include a clip that allows for attachment to clothing or articles of the user, or to simply place the device within a pocket or holder of the user. Accordingly, the physical contact 124 shown with respect to FIG. 1B can also be implemented upon the surface 120 of activity tracking device 100 of FIG. 1C. It should be understood, therefore, that the form factor of the activity tracking device 100 can take on various configurations and should not be limited to the example configurations provided herein.

Figure 2A:
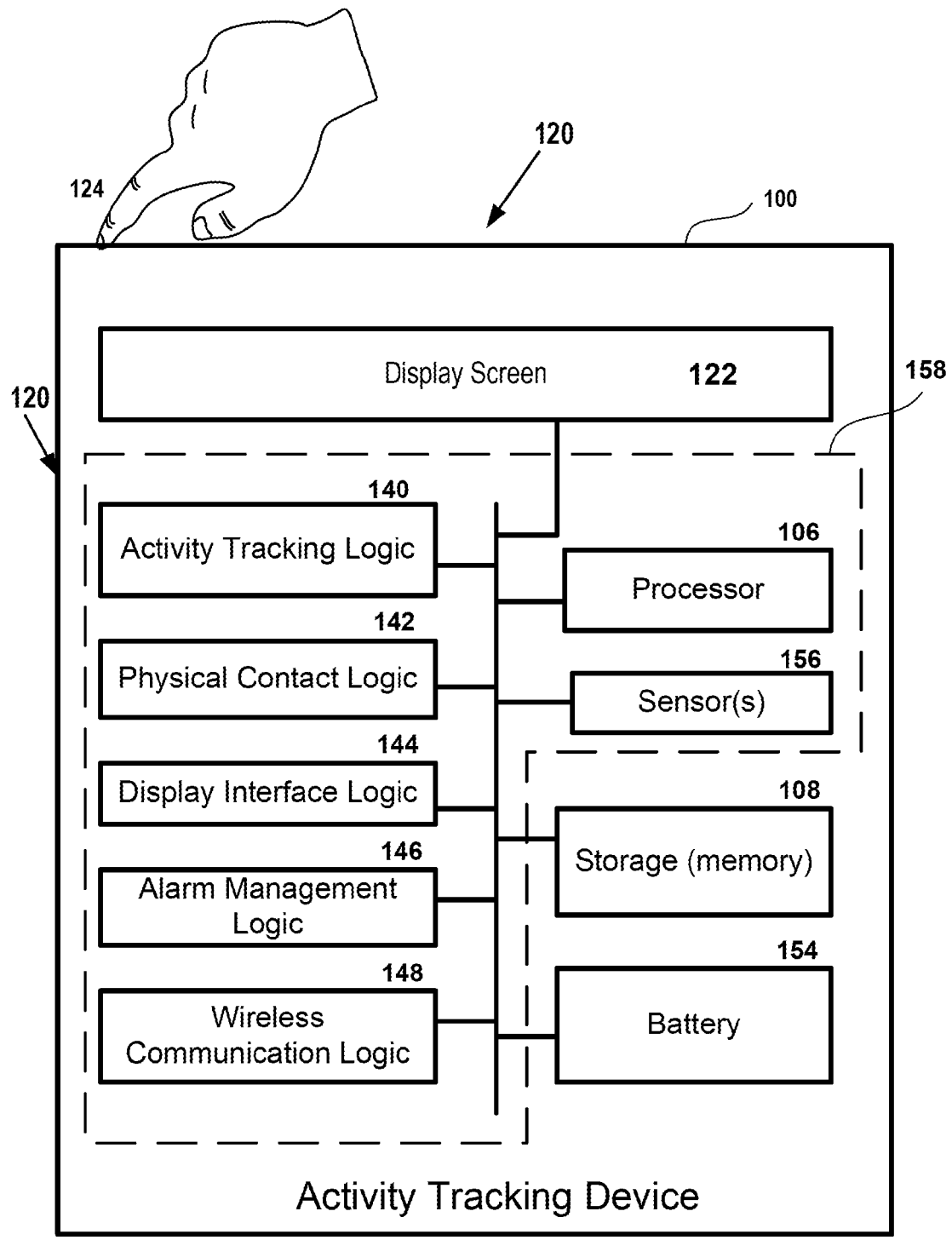
FIG. 2A illustrates an example of activity tracking device including example components utilized for tracking activity and motion of the device, and associated interfaces to a display screen, in accordance with one embodiment of the present invention.

FIG. 2A illustrates an example of activity tracking device 100 of FIG. 1A, showing some additional example components utilized for tracking activity and motion of the device, and associated interfaces to display screen 122. In this example, the finger of a user can be used to tap and provide physical contact 124 onto any surface 120 of activity tracking device 100. The physical contact, when sensed by sensors 156 of the activity tracking device 100, will cause a response by the activity tracking device 100, and therefore provide some metric on the display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 2A, the activity tracking device 100 includes logic 158. Logic 158 may include activity tracking logic 140, physical contact logic 142, display interface logic 144, alarm management logic 146, wireless communication logic 148, processor 106, and sensors 156. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be predefined to be a double tap input, and the physical contact logic 142 can analyze the motion to determine if a double tap indeed occurred in response to analyzing the sensor data produced by sensors 156.

In other embodiments, the physical contact logic can be programmed to determine when particular physical contacts occurred, the time in between the physical contacts, and whether the one or more physical contacts will qualify within predefined motion profiles that would indicate that an input is desired. If physical contact occurs that is not within some predefined profile or pattern, the physical contact logic will not indicate or qualify that physical contact as an input.

The display interface logic 144 is configured to interface with the processor and the physical contact logic to determine when specific metric data will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi signal, a Bluetooth signal, a low energy Bluetooth signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 2B:
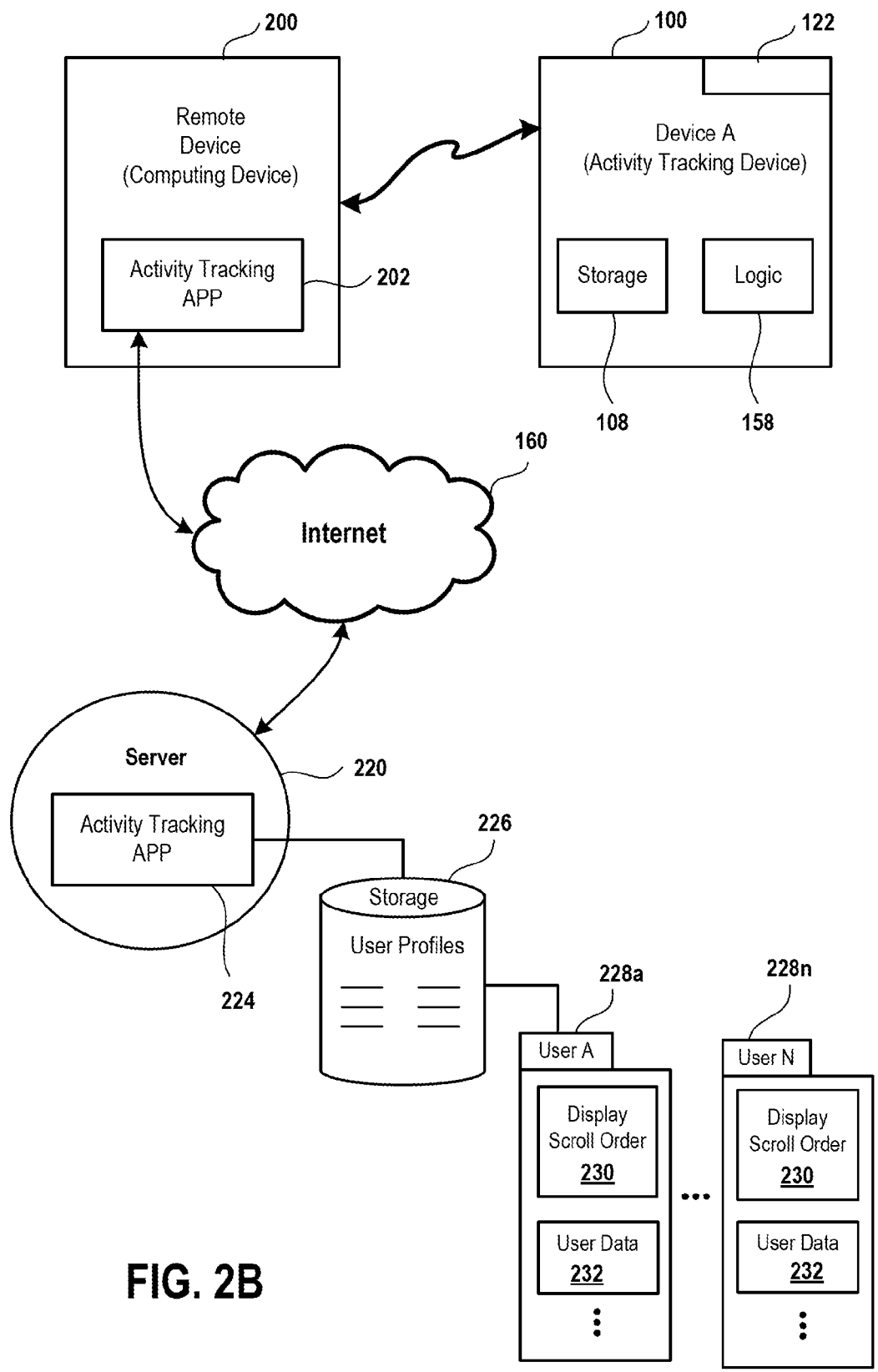
FIG. 2B illustrates an example of activity tracking device in communication with a remote device, in accordance with one embodiment of the present invention.

FIG. 2B illustrates an example of activity tracking device 100 in communication with a remote device 200. Remote device 200 is a computing device that is capable of communicating wirelessly with activity tracking device 100 and with the Internet 160. Remote device 200 can support installation and execution of applications. Such applications can include an activity tracking application 202. Activity tracking application 202 can be downloaded from a server. The server can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A and the Internet.

In one embodiment, remote device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi, and combinations thereof (such as connections to switches between different types of connection links). The remote device, as mentioned above, can be a smartphone or tablet computer, or any other type of computing device having access to the Internet and with capabilities for communicating with the activity tracking device 100.

A server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information can include, without limitation, data associated with a display scroll order 230, user data, etc. As will be described in greater detail below, the display scroll order 230 includes information regarding a user's preferences, settings, and configurations which are settable by the user or set by default at the server 220 when accessing a respective user account. The storage 226 will include any number of user profiles, depending on the number of registered users having user accounts for their respective activity tracking devices. It should also be noted that a single user account can have various or multiple devices associated therewith, and the multiple devices can be individually customized, managed and accessed by a user. In one embodiment, the server 220 provides access to a user to view the user data 232 associated with activity tracking device.

The data viewable by the user includes the tracked motion data, which is processed to identify a plurality of metrics associated with the motion data. The metrics are shown in various graphical user interfaces of a website enabled by the server 220. The website can include various pages with graphical user interfaces for rendering and displaying the various metrics for view by the user associated with the user account. In one embodiment, the website can also include interfaces that allow for data entry and configuration by the user.

The configurations can include defining which metrics will be displayed on the activity tracking device 100. In addition, the configurations can include identification of which metrics will be a first metric to be displayed on the activity tracking device. The first metric to be displayed by the activity tracking device can be in response to a user input at the activity tracked device 100. As noted above, the user input can be by way of physical contact. The physical contact is qualified by the processor and/or logic of the activity tracking device 100 to determine if the physical contact should be treated as an input. The input can trigger or cause the display screen of the activity tracking device 100 to be turned on to display a specific metric, that is selected by the user as the first metric to display. In another embodiment, the first metric displayed in response to the input can be predefined by the system as a default.

The configuration provided by the user by way of the server 220 and the activity management application 224 can also be provided by way of the activity tracking application 202 of the computing device 200. For example, the activity tracking application 202 can include a plurality of screens that also display metrics associated with the captured motion data of the activity tracking device 100. The activity tracking application 202 can also allow for user input and configuration at various graphical user interface screens to set and define which input will produce display of the first metric. In other embodiments, in addition to identifying the first metric to be displayed in response to the input, which may be physical contact, the configuration can allow an ordering of which metrics will be displayed in a specific scroll order.

In another embodiment, the scroll order of the metrics is predefined. In some embodiments, the input provided by the user by way of the physical contact can be pre-assigned to a specific metric in the scroll order. For example, the scroll order can remain the same, while the input can allow the screen to jump to a specific entry in the scroll order. Jumping to a specific entry can be viewed as a shortcut to a specific entry that is desired to be seen first by the user upon providing physical contact or input to the device 100.

Figure 3A:
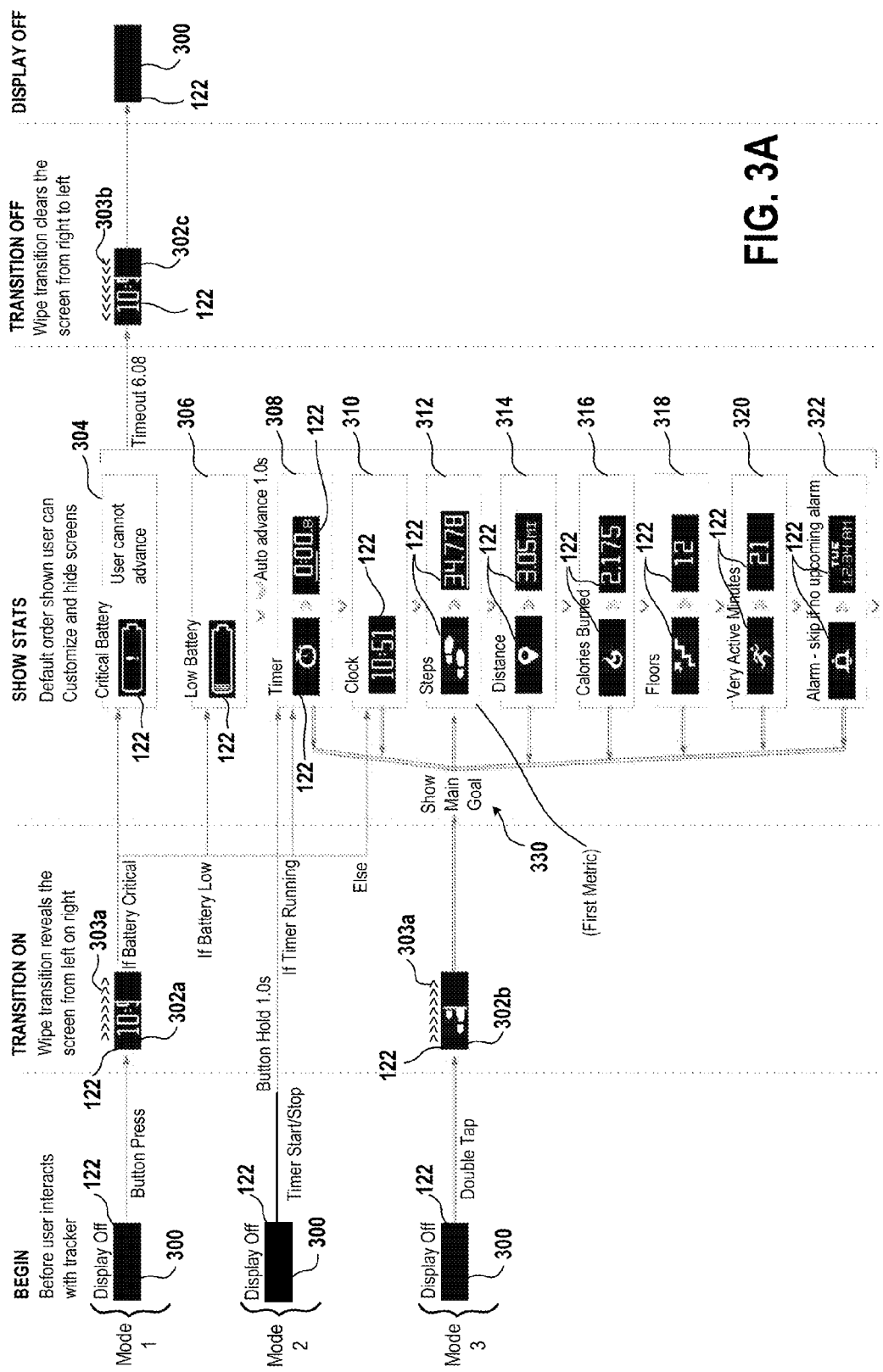
FIG. 3A illustrates a diagram of input interfaces for accessing screens that display metrics associated with the activity tracking device, in accordance with one embodiment of the present invention.

FIG. 3A illustrates a diagram of input interfaces for accessing screens that display metrics associated with the activity tracking device 100, in accordance with one embodiment of the present invention. As shown, the display screen 122 is in the off state before access is requested of the device 100. In one embodiment, the device 100 will shift to and off state when input is not received for a predetermined period of time, which allows the device 102 to save energy (i.e., battery power).

In mode 1, the display screen 122 is off 300 and upon a button press (e.g., of button 126 in FIG. 1B), the display screen 122 changes in transition 302a in direction 303a, to illustrate the time of day metric. However, if the battery is determined to be critical (e.g., the battery is too low to activate the device or operate it properly for a period of time), the display screen 122 will illustrate a graphic of a battery 304. The graphical battery 304 will indicate to the user that the device must be charged. If it is determined that the battery is low, a low battery indicator 306 will be shown in the display 122. The user can continue to use the device, but the critical battery notification may be re-displayed. After showing the low battery indicator 306, the display will advance to the clock metrics 310 after a predetermined period of time (e.g., 1 second). If it is determined that the timer function has been running, then the transition from the low battery indicator 306 would be automatic to the timer metric 308. Therefore, if the timer function is not running, the system will transition to the clock metrics 310, in this embodiment.

In mode 2, if it is determined that a button of the activity tracking device 100 had been pressed and held for a predetermined period of time (e.g., 1 second), then the transition would be directly to a timer metric 308. The timer metric 308 operates a stopwatch function, which first shows a graphic of a stopwatch and then automatically transitions to the time kept by the stopwatch function. If the user desires to transition from the timer metric 308 to one of the other metrics in the scroll order shown in FIG. 3A, the user can press the button 126 of the activity tracking device 100. For example, the downward facing arrow indicates that a button press will transition the display screen 122 to the next metric and so on. It should be understood that the downward facing arrow can also be activated by other than a button press, such as by physical contact (e.g., one or more taps onto the surface of the activity tracking device 100). As noted above, other input functions can also be provided, such as proximity sensing, touchscreens, voice activation, gesture detection, etc.

In mode 3, if it is determined that a double tap was detected on the surface of the activity tracking device 100 by a sensor, the display screen 122 will go from being on 302, to displaying a predetermined first metric. In this example, the predetermined first metric is a main goal 330 of the user, and is shown to be a step count metric 312. As shown, the display screen 122 will transition 302b in a direction 303a, which exposes an icon or graphic associated with the main goal 330, which is steps. The steps are shown as feet icon. The display screen 122, in one embodiment also transitions from the feet icon to the numerical value of the steps taken by the user utilizing the activity tracking device 100. If the user wishes to transition and view the other metrics in the scroll order, such as distance metric, calories burned metric, floors metric, very active minutes metric, alarm metric, the user can transition by pressing buttons 126 on the device 100. Again, transitioning downward (or through a list in any direction) is shown by the downward facing arrows, which are activated in response to a button press (or other types of inputs). These example transitions allow for display of other screens/data concerning metrics 308, 310, 312, 314, 316, 318, 320, 322, etc. It should be understood that additional metrics can be added to the scroll order, certain metrics can be deleted from the scroll order, the scroll order can be re-arranged, and these customizations can be made in response to user configurations or system configurations or default configurations.

After a predetermined period of time that no input is received by the activity tracking device 100, the display screen 122 will transition to and off state 300. The transition, in one embodiment allows for the display screen 122 to transition off 302c in direction 303b. Therefore, the display screen 122 will move to the off state 300 where battery consumption is reduced. In one embodiment, the transition to the off state 300 will occur after about 6 seconds. It should be understood that this predefined period of time can be modified for the specific configuration and should not be limited to the specific example. As will be described below with reference to FIG. 3D, one embodiment will allow for custom transitions between an off state to specific metrics based on the amount of time determined to have passed when no user input has been received.

Figure 3B:
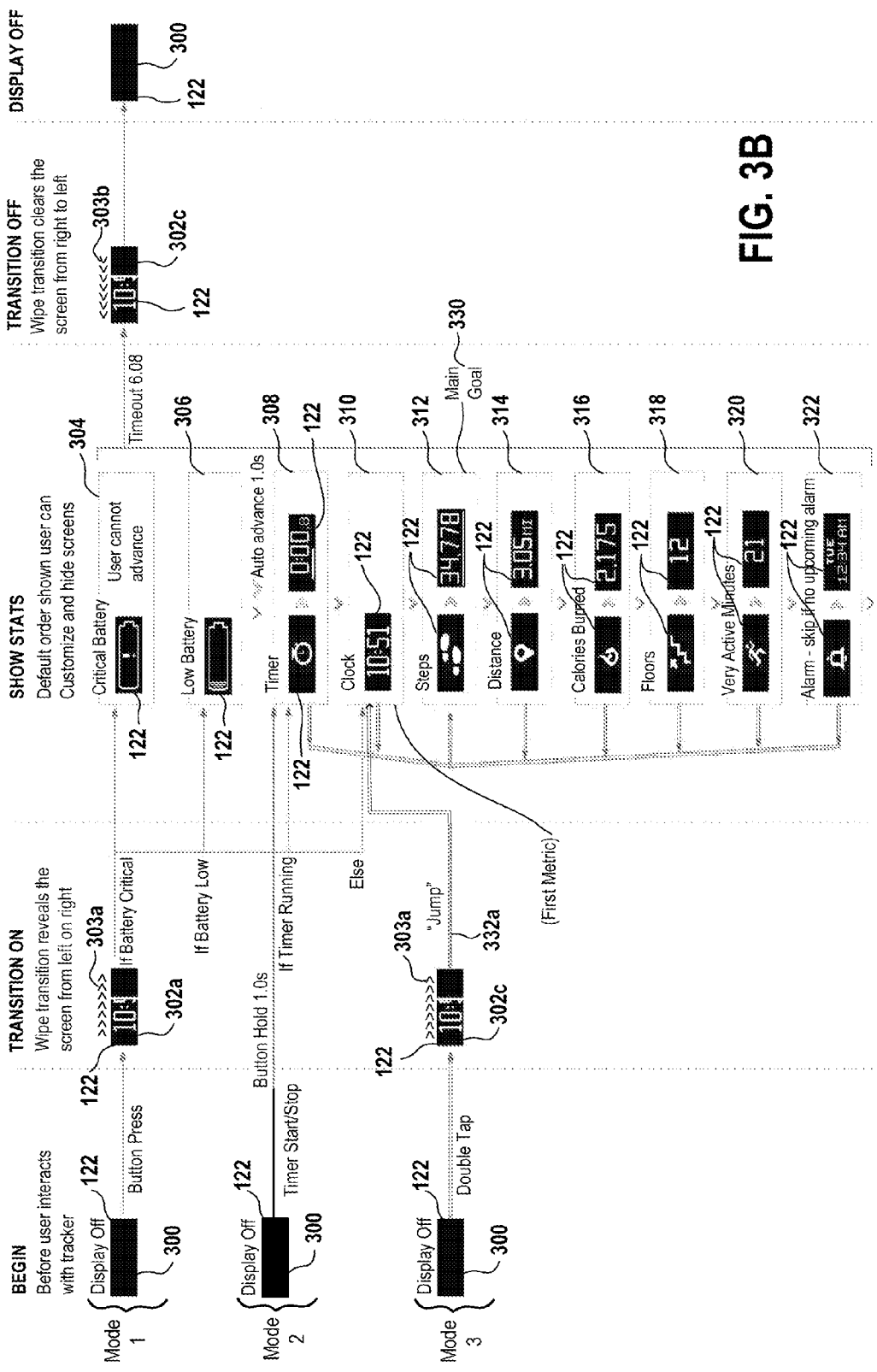
FIG. 3B illustrates an example where the activity tracking device has been programmed or customize by a user to select a specific metric to display on the display screen upon receiving input, in accordance with one embodiment of the present invention.

FIG. 3B illustrates an example where the activity tracking device 100 has been programmed or customize by a user to select a specific metric to display on the display screen 122 upon receiving input. In this example, the configuration has been made to the functionality of mode 3. In mode 3, the user has configured a double tap (physical contact) detected to activate or jump to a specific metric selected by the user. In this example, the user has selected that a double tap input will cause the display screen 122 to transition from off state 302 to the clock metric 310. This will jump 332a, in the scroll order, to the clock metric 310. The clock metric 310 will be considered the first metric, of a plurality of metrics to be displayed on the display screen 122 of the activity tracking device, in response to a double tap. Once the device jumps to display the clock metric 310, the user can then scroll through the remaining metrics by selecting or pressing a button 126 of the activity tracking device 100. As noted above, transition to the other metrics can also be enabled by additional physical contact or non-physical contact inputs.

Figure 3C:
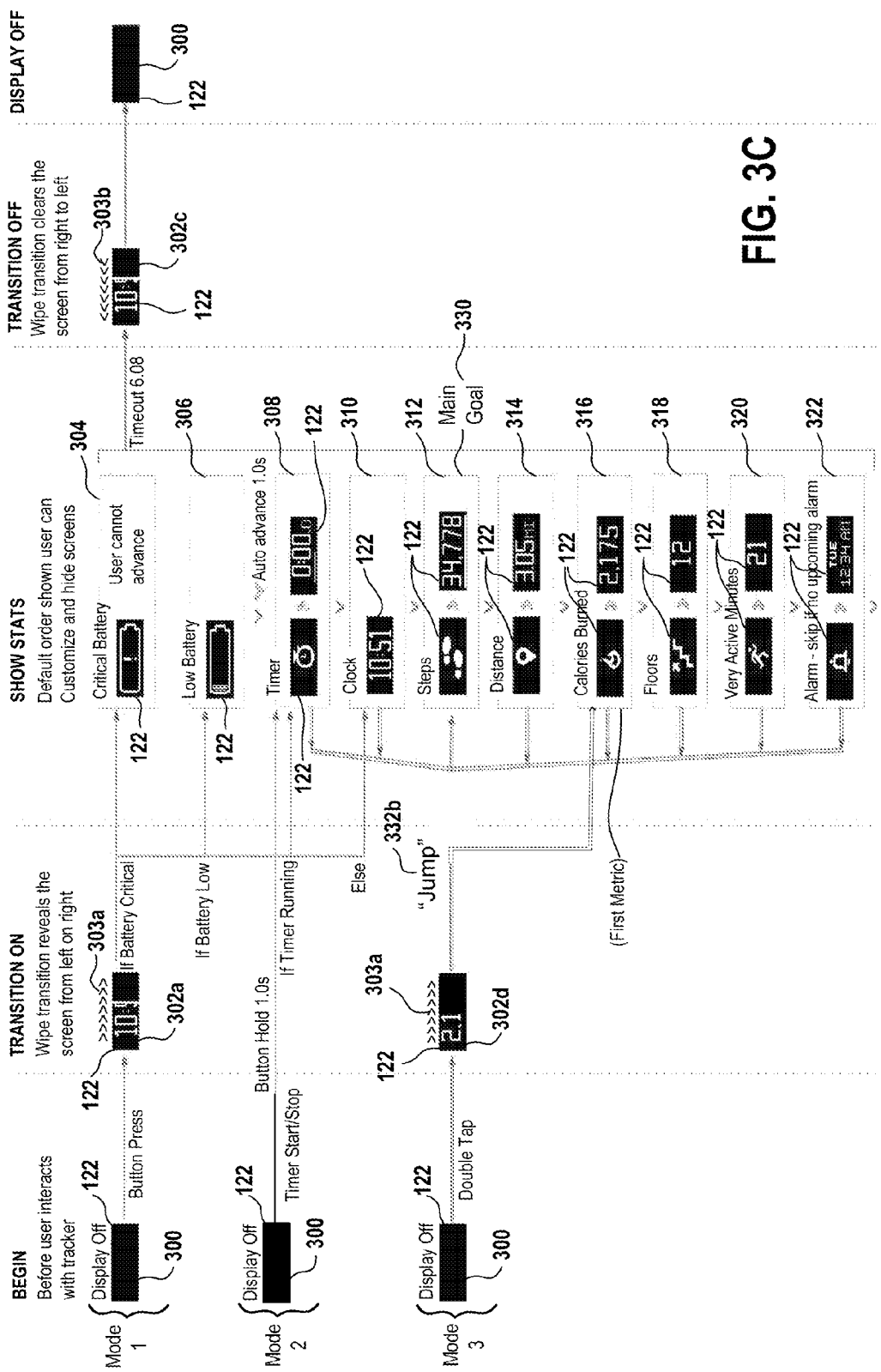
FIG. 3C illustrates another example where the activity tracking device 100 has been programmed or customize by a user to select a different metric to be the first metric, in accordance with one embodiment of the present invention.

FIG. 3C illustrates another example where the activity tracking device 100 has been programmed or customize by a user to select a different metric to be the first metric. The first metric is a metric that will be displayed on the display screen 122 upon receiving the input, in accordance with mode 3. In this example, mode 3 is a transition from the off state 300 to display the first metric in response to a double tap. Although specific mention of a double tap is provided herein, it should be understood that any number of caps can be provided to qualify as the physical contact sensed by a sensor of the device 100. Once the double tap is received, the display screen of the activity tracking device 100 will jump 332b to calories burned metric 316. Calories burned metric 316 is a metric that the user has configured to be the first metric that will be displayed upon receiving a double tap when the display was in an off state. By way of this illustration, it should be understood that any one of the metrics can be configured to be the first metric that is shown on the display screen 122 upon receiving the double tap. A user can then transition to other metrics in the scroll order or list of metrics by providing additional input. The downward facing arrow between the metrics shows the transition through the various metrics. Upon displaying each of the metrics, in one embodiment, the display screen 122 will display a graphic icon indicative of the type of metric that will be displayed. The right facing arrow indicates that the transition between the graphic icons to the numerical metrics will be automatically transitioned without additional user input.

Figure 3D:
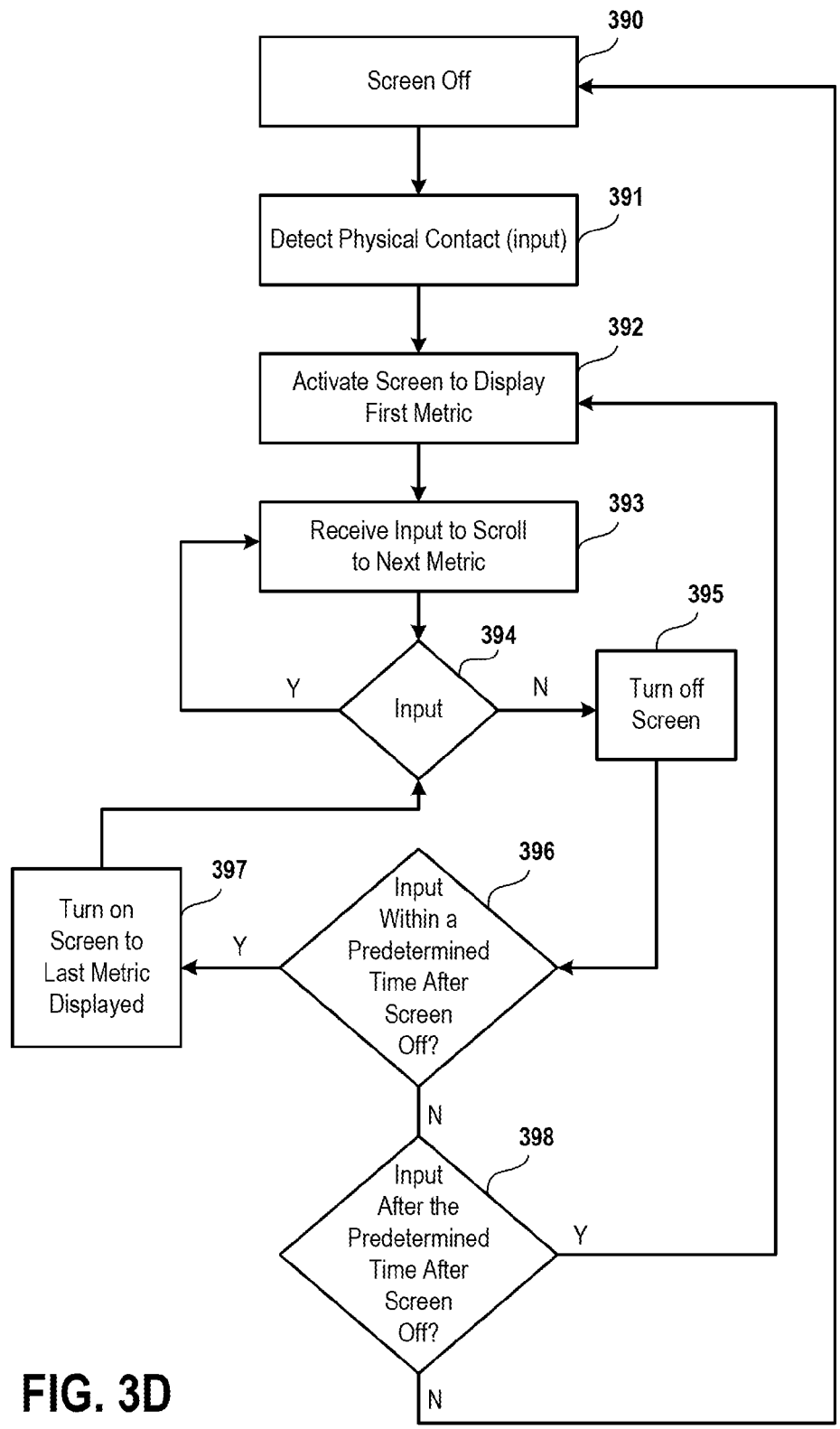
FIG. 3D illustrates a flowchart defining example interactivity and display functionality of the activity tracking device, in accordance with one embodiment of the present invention.

FIG. 3D illustrates a flowchart defining example interactivity and display functionality of the activity tracking device 100, in accordance with one embodiment of the present invention. In one embodiment, the screen is in an off state in operation 390. In operation 391, physical contact or input is detected by the activity tracking device 100. The physical contact or input, as defined above can include taps, touches, proximity, button pushes, etc. Once the input is detected in operation 391, the display screen of the device will be activated to show the first metric. As described above, the first metric can be user configured so as to allow selection of which metric will be displayed first upon receiving the input. In operation 393, it is determined if additional input is received to scroll or move to the next metric.

If additional input is received in operation 394, the display screen will move in scroll to the next metric. This will continue as the user is allowed to select the next metric in the list or scroll order. In one embodiment, the scroll order can wrap around and continue to display metrics. If no input is received for a period of time, the display screen will turn off in operation 395. In operation 396, it is determined if input is received within a predetermined amount of time after the screen was turned off. For example, if input, such as a button press is received within 3 seconds of the screen turning off, the screen will turn back on and display the last metric that had been displayed.

For instance, in FIG. 3A, if the last metric being viewed was calories burned 316, and no input was received, the screen will turn off. If within 3 seconds of the screen being off a button press is detected, the calories burned metric 316 will be displayed once again in operation 397. The method will then proceed back to operation 394 where it is determined if additional input is received to transition to view a next metric 393. If no input is received after a predetermined amount of time since the screen was off in operation 396, the method will transition to operation 398. In operation 398 it is determined that input occurred after the predetermined amount of time that the screen was off, the method will return back to activate the screen and show the first metric. The input received in operation 398 may be a button press or a physical contact, such as input received through mode 1 or mode 3. If after the predetermined amount of time that the screen was off no input was received, the screen will transition back or remain in the off state 390.

Figure 3E:
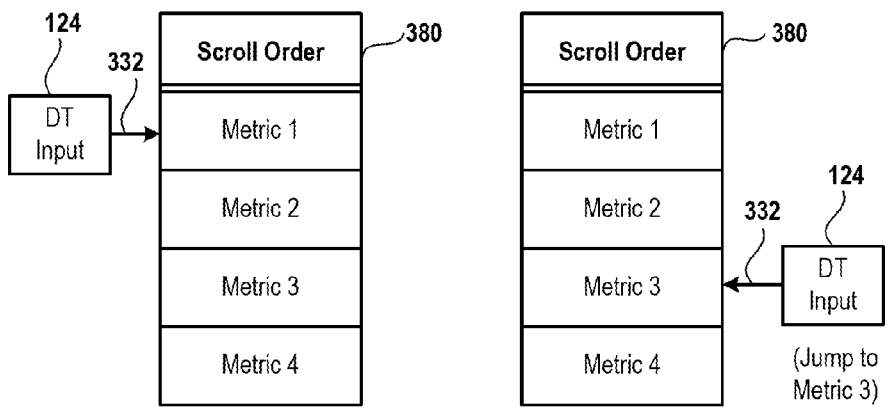
FIG. 3E illustrates an example of a table showing example scroll orders and inputs, in accordance with one embodiment of the present invention.

FIG. 3E illustrates an example of a table 350 showing example scroll order 352 and input 354. In this example, the scroll order will include screen off 300, clock metric 310, distance metric 314, calories burned metric 316, floors metric 318, very active minutes metric 320, alarm metric 322. In this example, when no physical contact qualifying as an input is received, the screen will remain off. This of course also includes receiving no button presses so that the screen will remain off. In this example, a double tap (DT) physical contact 124 will activate the display screen 122 with the first metric, which is identified by the user to be the clock metric 310. The user can then transition by various button presses 126a to the various metrics in the scroll order after receiving each of the button presses. As noted above, instead of button presses other input can also be used to transition between the metrics.

FIG. 3F illustrates an example of the scroll order 380 that extends from metric 1 to metric 4. In this example, the first metric has been identified to be metric 1. Additionally, a double tap input is predefined to access metric 1 as the initially displayed metric on the activity tracking device. FIG. 3G illustrates an example where metric 3 is designated as the first metric, which will be the metric data displayed initially upon receiving the double tap input 124. The custom designation of the first metric to any one of the metrics in the scroll order functions as a jump 332 to the specific metric identified by the user. The specific metric identified as the first metric can also be predefined by the system or set as a default. As used herein, a jump should be interpreted to also include a shortcut to a specific metric in a list.

Figures 1, 4A:
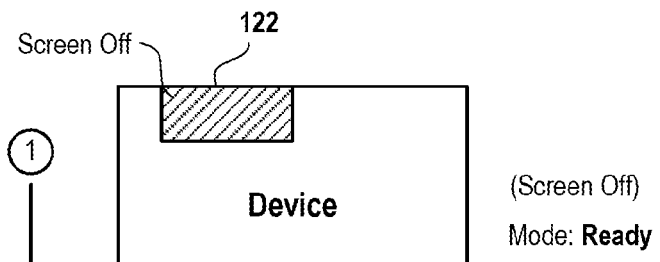
FIG. 4A-1 illustrates an example in accordance with an alternative embodiment, associated with navigating the screens of an activity tracking device showing ready mode.
Figures 2, 4A:
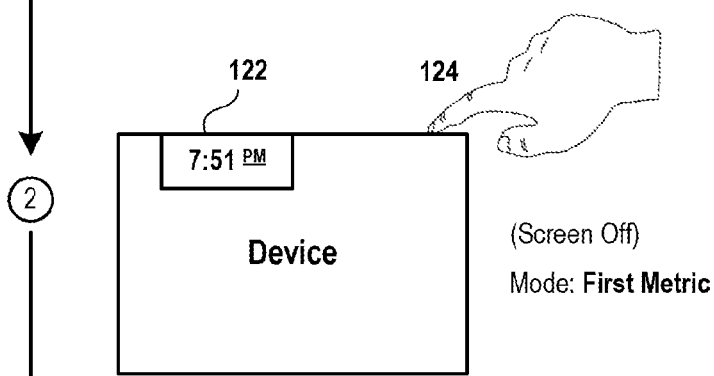
Figures 3, 4A:
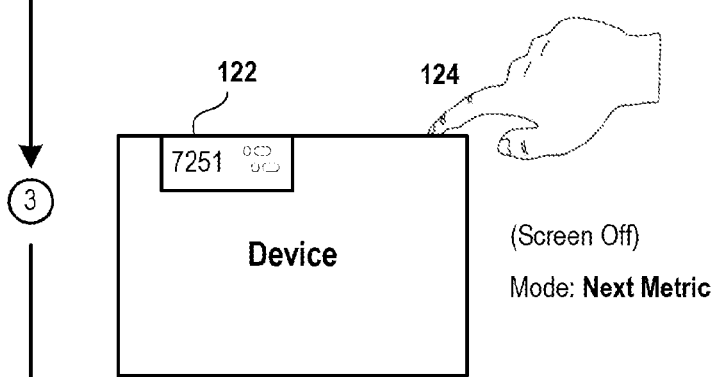
Figure 4B:
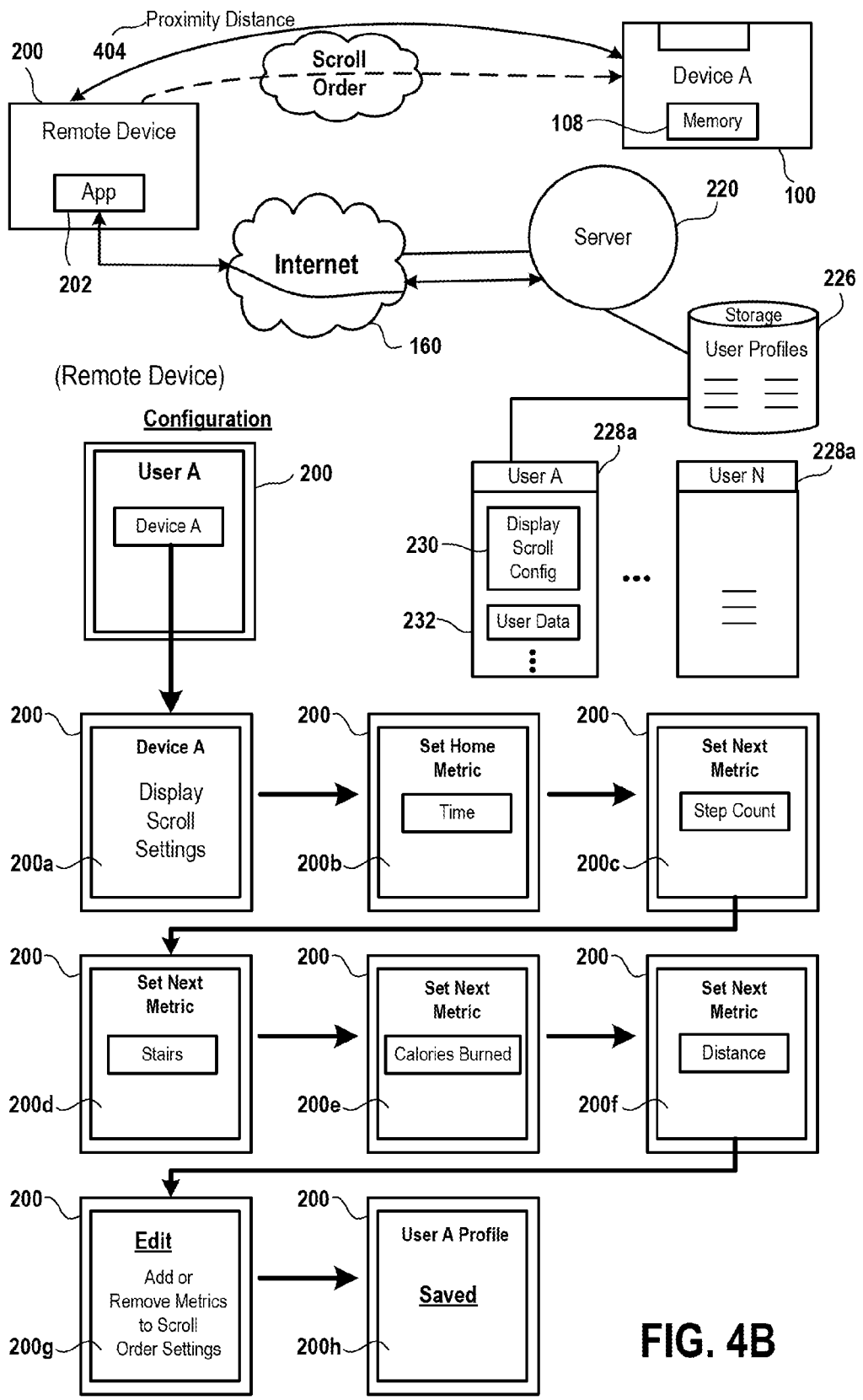
FIG. 4B illustrates an example of a system that includes the device, a remote device, and the server interfacing over the Internet, in accordance with one embodiment of the present invention.
Figures 5, 6:
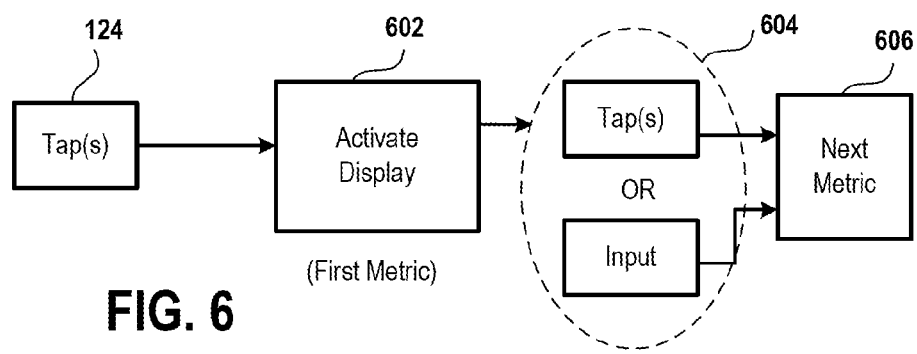

FIGS. 4A-1 to 4A-8 illustrate examples in accordance with an alternative embodiment, associated with navigating the screens of activity tracking device 100. In this example, that device 100 has a screen 122 that is in the off state. In FIG. 4A-1, the screen is in an off state, which may indicate that the device is in a ready mode and ready to receive input. In FIG. 4A-2, the device receives physical contact 124, which may be a double tap. The physical contact and 24 will activate the display screen 122 and display a first metric. In this example the first metric is the time of day. In FIG. 4A-3, additional physical contact is received by device 100 which causes the display screen 122 to show a next metric, which in this example is step count. In FIG. 4A-4, the device 100 has received another double tap 124 which then causes the display screen 122 to show a next metric. This next metric is a step count. In FIG. 4A-5, the device receives another physical contact 124 which causes the device to illustrate a next metric. The next metric is calories burned. In FIG. 4A-6, the device receives another physical contact 124 which causes the display screen 122 to show a next metric. The next metric is a distance. In FIG. 4A-7, it is determined that no physical contact has occurred for a predetermined period of time 402. This will cause the device 100, as shown in FIG. 4A-8, to transition to turn off the screen, and back to the ready mode.

FIG. 4B illustrates an example of a system that includes the device 100, a remote device 200, and the server 220 interfacing over the Internet 160. The interfacing allows for the remote device 200 to set the specific configuration of the scroll order settings of device 100, in accordance with a user configuration. In this example, using the remote device 200, the user navigates to a screen provided by the application 202 of the remote device. The application 202 is an activity tracking application that can communicate with activity monsoon application 224 managed by the server 220. As discussed above with reference to FIG. 2B, activity tracking application 202 can include a plurality of user interfaces and screens to allow user input and access to the activity data or configure settings.

The settings being configured in this example includes settings associated with the scroll order and the definition of the first metric. In this example, the activity tracking application 202 will allow the user to login to his or her user accounts and access and identify device a, which is the activity tracking device 100. Using screens and menus provided by the activity tracking application, the user is able to identify the display scroll order settings in the screen 200a of the device 100. In this example, the user has decided to set the home screen metric (e.g. first metric), as time or clock. Optionally, the user may then select the scroll order of the various screens or GUIs (e.g., screens 200a-200h) to be traversed. In this example, the user has selected step count metric to follow, then stairs metric, then calories burned metric, and then distance metric. The user may also be prompted or can elect to edit, remove or add additional metrics to the scroll order setting. Once the user approves of the settings, the user can save the settings to the user profile. Saving the settings to the user profile can act to update the settings to the user display scroll order configuration 230 in the user account (user A). This configuration setting is synchronized with the server 220 and then transferred to the device 100 by way of a wireless connection over a predefined proximity distance 404. As noted above, in one embodiment, communication between the device 100 and the remote device 200 (computing device) is by way of a wireless link. The wireless link may be, for example Bluetooth radio communication, and in one embodiment, low-energy Bluetooth radio communication.

FIG. 5 illustrates a table providing a scroll order 352 and the various inputs 354 that can be defined to traversed the scroll order, in one embodiment. In this embodiment, the screen is off 300 and ready for use. When the screen is off, the device is on and operating, but energy to power the screen does not consume battery power. In this state, no physical contact has been received during a period of time. When a double tap is received, the configuration will allow the screen to transition to a first metric, which is the time of day. As noted above, the first metric can be defined to be any one of the metrics in the scroll order. Additionally, the scroll order can remain in the same order yet the first metric can be identified as any one of the metrics in the scroll order, and access to the specific metric can be by way of a jump or shortcut. In another embodiment, the scroll order configuration can be reordered. In this example, transitioning from metric to next metric is by way of double tap (DT) physical contact. However as noted above, the transitioning between the metrics can be by way of any number of inputs, such as physical and nonphysical interfaces, voice communication, proximity communication, button presses, etc.

FIG. 6 illustrates an example of a physical contact 124 represented by taps, which act to activate the display 602 in a first metric. The next input can be an additional tap or another suitable input 604, to transition to the next metric 606.

Figure 7:
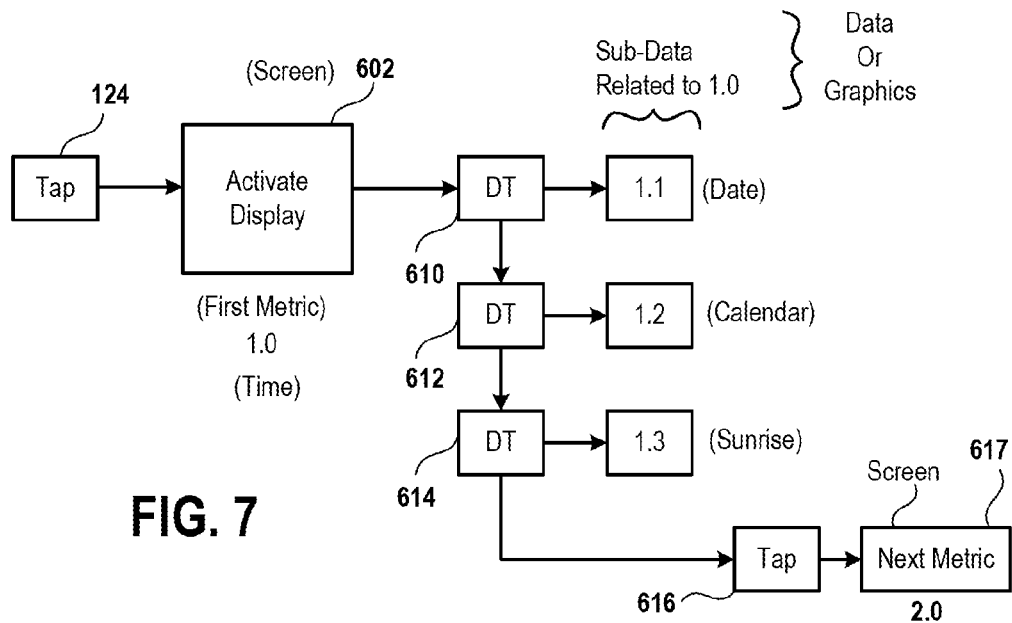

FIG. 7 illustrates another example where a single tap 124 activates the display 602 in the first metric. In this example, the first metric 1.0 is time. If within a period of time a double tap is received 610, a sub-data metric 1.1 can be displayed. Sub-data metric can be an additional metric that further describes or provides additional information related to the first metric. For example, sub-data metric 1.1 can be the date. Another double tap 612 can provide sub metric 1.2 which can be a calendar. Another double tap 614 can provide another sub metric 1.3, which can be sunrise metrics. A single tap 616 can then provide the next metric 2.0, which will define the metric data 617 associated with that next metric. Accordingly, it should be understood that a specific metric can have additional information (e.g., multiple levels of information or formats) that relate to that same metric, and that additional information can be provided by additional screen displays of metric data that relate to one of the metrics.

Figure 8:
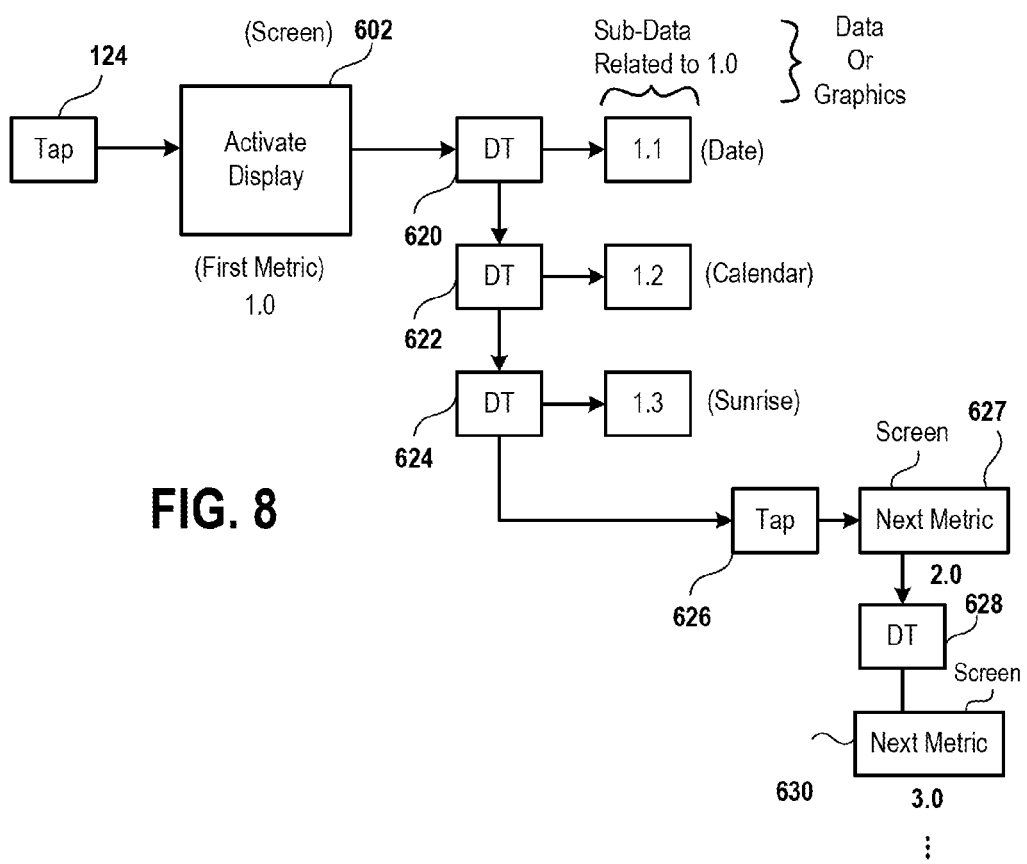

FIG. 8 illustrates an example of a double tap physical contact 124 acting to initiate the display 602 with the first metric 1.0. A single tap 620 can then expose or present sub-data 1.1, single tap 622 can present sub-data 1.2, single tap 624 can present sub-data 1.3. Similar to FIG. 7, the provides additional data/information regarding a specific metric. However, in FIG. 8, the transitions between the sub-data screens are by way of a single tap, as opposed to a double tap. Thus a double tap 626 can then expose a next metric 627, shown as metric 2.0. Metric 2.0 can also have sub-data (not shown). Another double tap 626 can then expose the next metric 630, shown as metric 3.0. Each of the various metrics organized in a scroll order can have sub-data associated therewith, if desired for the specific configuration. These examples are provided to show that physical contact input can be configured and quantified to define a specific input for traversing a specific display screen, or selecting specific metrics to show in specific screen displays.

In some embodiments, a device is provided. The device is defined in a form of a wearable wrist attachable structure. In one embodiment, the device has a housing that is at least partially constructed or formed from a plastic material. In one embodiment, the housing of the device includes an altimeter. The defines can further include a transiently visible display, or a dead-front display, a touch screen display, a monochrome display, a digital display, a color display, or combination thereof. In yet another embodiment, the device can include one or more accelerometers. In one specific example, the device can include a 3-axis accelerometer. On still another embodiment, a 3-axis accelerometer can be replaced with or replicated by use of separate accelerometers (e.g., 3 accelerometers) positioned orthogonally to each other.

Figure 9:
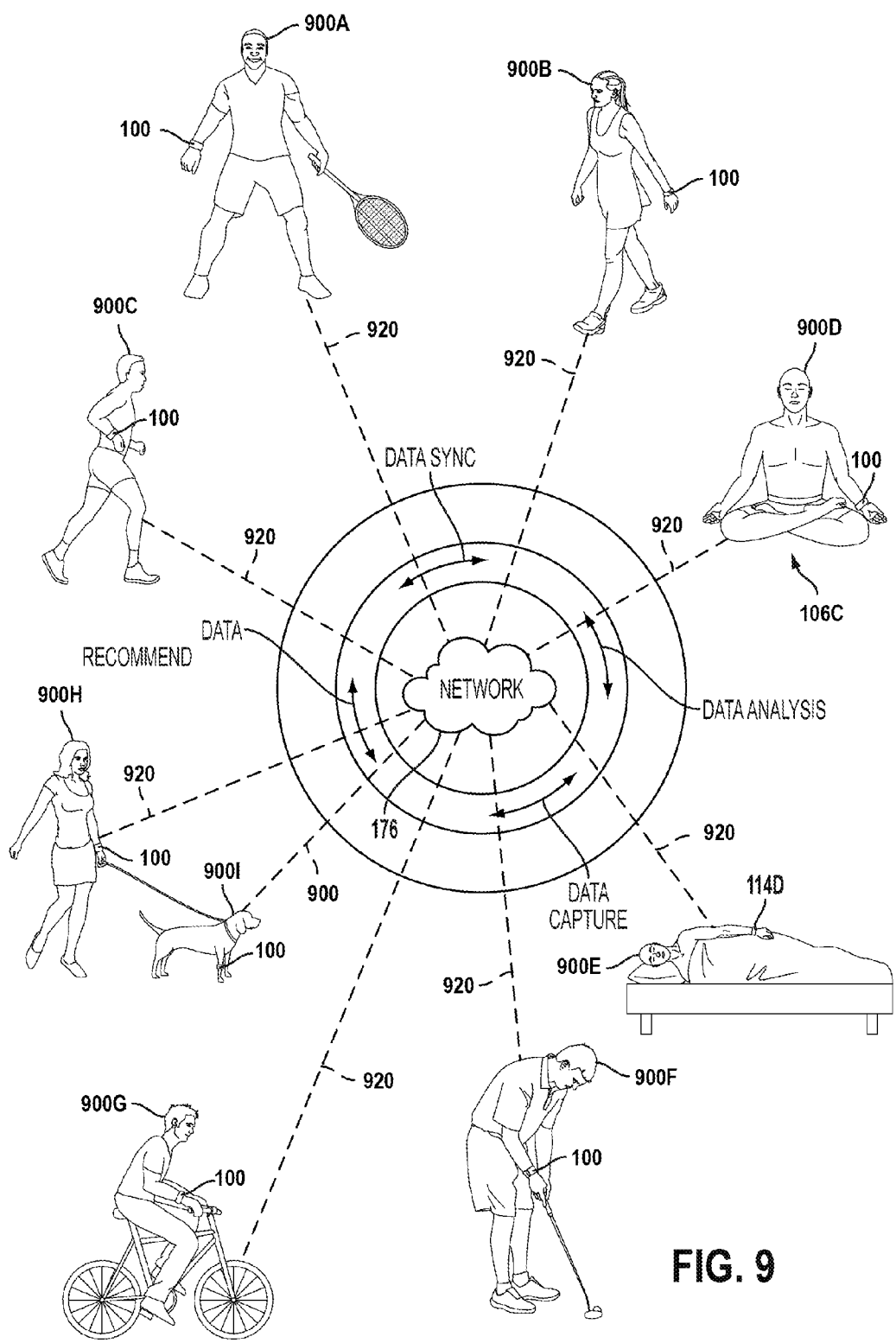
FIG. 9 illustrates an example where various types of activities of users 900A-900I can be captured or collected by activity tracking devices, in accordance with various embodiments of the present invention.

FIG. 9 illustrates an example where various types of activities of users 900A-900I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 920 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user.

For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g. smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method, comprising,
    detecting a physical contact by a sensor of a device that is configured to display a plurality of metrics on a screen of the device, the physical contact being to a surface of a housing of the device that includes the sensor, the sensor additionally being used to detect activity data;
    examining the physical contact to determine if the physical contact qualifies as an input for the device, wherein the physical contact qualifies as the input when a motion profile detected by the sensor in response to the physical contact is determined to be within a predefined profile that is indicative of the input, wherein the examining of the motion profile includes determining if the physical contact is the input for the device or is activity data, as the sensor is used to detect the physical contact and the activity data;
    maintaining the screen of the device in an off state for physical contact that does not qualify as the input; and
    activating the screen of the device to display a first metric when the examining determines that the physical contact qualifies as the input;
    wherein the physical contact that qualifies as the input causes a jump to display the first metric and the activating of the screen of the device occurs without requiring an additional user input, wherein the method is executed by a processor.

2. The method of claim 1, wherein, (a) the first metric is a time metric and a remainder of the plurality of metrics define activity data of a user as captured over time by the device, or (b) the first metric is other than a time metric.

3. The method of claim 2, wherein the plurality of metrics are configured to a scroll order, such that each metric is displayed on the screen in succession in response to successively detected physical contact that qualifies as the input.

4. The method of claim 1, wherein a scroll order of the plurality of metrics is user configurable.

5. The method of claim 4, wherein,
    additional metrics or fewer metrics are user configurable to be part of the plurality of metrics, and
    a position of each metric in the scroll order is user configurable.

6. The method of claim 1, wherein the first metric is configurable to be a selected metric of the plurality of metrics that are arranged in a scroll order.

7. The method of claim 1, further comprising,
    in response to a user input being detected, transitioning from the first metric to a next metric in a scroll order or to an off state when no user input is detected; and
    if user input is received within a predetermined time after the off state, turning the screen on and displaying the last displayed metric, or if the user input is received after the predetermined time after the off state, turning the screen on and displaying the first metric.

8. The method of claim 1, wherein the plurality of metrics include a time of day metric and metrics representing activity data captured by the device when associated with a user, the activity data being of the user.

9. The method of claim 1, wherein the plurality of metrics are configured in a scroll order, and further comprising,
    transitioning, after the first metric, in the scroll order on the screen of the device in response to one or more user inputs;
    wherein in response to the physical contact that qualifies as the input, a shortcut transition is made back to the first metric for display on the screen of the device.

10. The method of claim 1, further comprising,
    transitioning the screen to an off state in an absence of user input to the device;
    activating the screen in response to physical contact that qualifies as the input; and
    displaying the first metric on the screen in response to the input.

11. The method of claim 1, wherein the physical contact includes tap contact that is identified by the sensor of the device, the sensor producing motion data that is examined to qualify the motion data as the input.

12. The method of claim 1, wherein the physical contact that qualifies as the input is one tap, or a double tap, or a set of taps, or a pattern of taps, or a plurality of taps repeated within a predefined frequency.

13. The method of claim 1, wherein the plurality of metrics are defined by one or more of time of day data, timer data, alarm data, measurement data of the user, and activity data of a user as tracked or captured by the device.

14. A device configured for capture of activity data for a user, comprising,
- a housing;
- a screen disposed on the housing to display a plurality of metrics which include metrics that characterize the activity data captured over time;
- a sensor disposed in the housing to capture physical contact upon a surface of the housing, and capture the activity data; and
- a processor to process the physical contact to determine if the physical contact qualifies as an input, wherein the processor determines that the physical contact qualifies as the input when a motion profile detected by the sensor in response to the physical contact is determined to be within a predefined profile that is indicative of the input, wherein the motion profile being within the predefined profile distinguishes the motion profile from captured activity data by the sensor, as the sensor is used to capture both the physical contact and the activity data, the processor enabling the screen to an on state when the physical contact qualifies as the input, the physical contact being qualified as the input without requiring an additional user input, the screen configured to display one or more of the plurality of metrics in accordance with a scroll order, a first metric of the plurality of metrics being displayed in accordance with user configuration identifying that the first metric is to be displayed in response to the physical contact that qualifies as the input, as determined by the processor.

15. The device of claim 14, wherein the housing further includes memory for storing the activity data, captured data, and wireless communication logic.

16. The device of claim 15, wherein the wireless communication logic includes one of WiFi processing logic, or Bluetooth (BT) processing logic, or radio processing logic.

17. The device of claim 16, wherein the wireless communication logic is configured to pair with a portable computing device or a computer, and the portable computing device or the computer is configured for communication over the Internet with a server, the server having processing instructions for configuring the first metric that is accessed by the input, and each metric in the scroll order and processing instructions for adding and removing metrics from the list of metrics.

18. The device of claim 14, wherein one of the plurality of metrics is a time of day metric.

19. The device of claim 18, wherein the first metric is the time of day metric, or any one of the metrics in the scroll order.

20. The device of claim 14, wherein the housing is part of a wearable wrist attachable structure, or an attachable structure that can be carried or worn by the user.

21. The device of claim 14, wherein the physical contact captured by the sensor is from one or more taps upon the housing by a finger or hand.

22. The device of claim 14, wherein the user configuration identifying the first metric enables a jump to define any metric in the scroll order as the first metric.

23. The device of claim 14, wherein each metric in the scroll order is user configurable, and metrics are configured to be added or removed from a list of metrics in the scroll order.

24. The device of claim 14, wherein the housing includes a button.

25. The device of claim 14, further comprising one or both of an altimeter and an accelerometer.

26. A computer readable medium, being non-transitory, for storing program instructions executable by a processor, the computer readable medium comprising,
- program instructions for detecting a physical contact by a sensor of a device that is configured to display a plurality of metrics on a screen of the device, the physical contact being to a surface of a housing of the device that includes the sensor, the sensor additionally being used to detect activity data;
- program instructions for examining the physical contact to determine if the physical contact qualifies as an input for the device, wherein the physical contact qualifies as the input when a motion profile detected by the sensor in response to the physical contact is determined to be within a predefined profile that indicates the input, wherein the examining of the motion profile includes determining if the physical contact is the input for the device or is activity data, as the sensor is used to detect the physical contact and the activity data;
- program instructions for maintaining the screen of the device in an off state for physical contact that does not qualify as the input; and
- program instructions for activating the screen of the device to display a first metric when the examining determines that the physical contact qualifies as the input, the physical contact being qualified as the input without requiring an additional user input,
- program instructions for detecting user input to transition from the first metric to a next metric in a scroll order or to an off state, and
- if user input is received within a predetermined time after the off state, turning the screen on and displaying the last displayed metric, and if the user input is received after the predetermined time after the off state, turning the screen on and displaying the first metric, wherein the plurality of metrics include a time of day metric and metrics representing activity data captured by the device when associated with a user, the activity data being of the user.

27. The computer readable medium of claim 26, wherein, the input is associated with qualified physical contact, and
the user input is associated with one of qualified physical contact, or non-touch proximity input, or voice input, or button press input.

28. An activity tracking device configured for capturing activity data for a user, comprising,
- a housing configured as a wearable wrist attachable structure;
- a screen disposed on the housing to display a plurality of metrics which include metrics that characterize the activity data captured over time;
- an accelerometer sensor disposed in the housing to capture physical contact upon a surface of the housing and capture activity data; and
- a processor to process the physical contact to determine if the physical contact qualifies as an input, wherein the physical contact qualifies as the input when a motion profile detected by the accelerometer sensor in response to the physical contact is determined to be within a predefined profile that is indicative of the input, wherein the motion profile being within the predefined profile distinguishes the physical contact from the activity data, as the accelerometer is used to capture both the physical contact and the activity data, the processor enabling the screen from an off state when the physical contact qualifies as the input, the physical contact being qualified as the input without requiring an additional user input the screen configured to display one or more of the plurality of metrics in accordance with a scroll order, a first metric of the plurality of metrics being displayed in accordance with user configuration identifying that the first metric is to be displayed in response to the physical contact that qualifies as the input, as determined by the processor, wherein the physical contact captured by the accelerometer sensor is from sensing or detecting one or more taps producing the predefined profile upon the surface of the housing by a finger, or hand or object, wherein the user configuration identifying the first metric enables setting of a shortcut to any metric in the scroll order to be the first metric.

* * * * *